United States Patent
Dröge et al.

(10) Patent No.: US 7,846,732 B2
(45) Date of Patent: *Dec. 7, 2010

(54) SEQUENCE SPECIFIC DNA RECOMBINATION IN EUKARYOTIC CELLS

(75) Inventors: Peter Dröge, 100 Nanyang Crescent Meadows # 11-01, Singapore (SG) 637819; Barbara Enenkel, Warthausen (DE)

(73) Assignees: Peter Dröge, Singapore (SG); Boehringer Ingelheim Pharma KG, Rhein (DE)

( * ) Notice: Subject to any disclaimer, the term of this patent is extended or adjusted under 35 U.S.C. 154(b) by 146 days.

This patent is subject to a terminal disclaimer.

(21) Appl. No.: 11/281,945

(22) Filed: Nov. 17, 2005

(65) Prior Publication Data

US 2006/0078968 A1 Apr. 13, 2006

(51) Int. Cl.
- *C12N 15/87* (2006.01)
- *C12N 15/90* (2006.01)
- *C12N 5/00* (2006.01)
- *C12N 15/00* (2006.01)
- *C12P 21/00* (2006.01)

(52) U.S. Cl. ............ 435/462; 435/325; 435/69.1; 435/455

(58) Field of Classification Search .............. None
See application file for complete search history.

(56) References Cited

U.S. PATENT DOCUMENTS

| 2002/0007051 A1 | 1/2002 | Cheo et al. ........... 536/23.1 |
| 2003/0027337 A1 | 2/2003 | Droge et al. ........... 435/456 |
| 2003/0226164 A1 | 12/2003 | Suttie et al. ........... 800/278 |

FOREIGN PATENT DOCUMENTS

WO WO 01/16345 3/2001

OTHER PUBLICATIONS

Christ and Dröge, "Alterations in the directionality of λ site-specific recombination catalyzed by mutant integrases in vivo," *J. Mol. Biol.*, 288:825-836, 1999.
Christ and Droge, "Alterations in the directionality of lambda site-specific recombination catalyzed by mutant integrasses in vivo," *J. Mol. Biol.* 288:825-836, 1998.
Christ and Dröge, "Genetic manipulation of mouse embryonic stem cells by mutant λ integrase," *Genesis*, 32:203-208, 2002.
Christ et al., "Site-specific recombination in eukaryotic cells mediated by mutant λ integrases: implications for synaptic complex formation and the reactivity of episomal DNA segments," *J. Mol. Biol.*, 319:305-314, 2002.
Gu et al., "Deletion of a DNA polymerase β gene segment in T cells using cell type-specific gene targeting," Science, 265:103-106, 1994.
Hoess et al., "Mechanism of strand cleavage and exchange in the Cre-lox site-specific recombination system," *J. Mol. Biol.*, 181:351-362, 1985.
Jefferis, "Glycosylation of human IgG antibodies relevance to therapeutic applications," *BioParm*, pp. 1-6, 2001.
Kilby et al., "Site-specific recombinases: tools for genome engineering," *Trends Genet.*, 9:413-421, 1993.
Kühn et al., "Inducible gene targeting in mice," Science, 269:1427-1429, 1995.
Lorbach et al. "Site-specific recombination in human cells catalyzed by phage lambda integrase mutants," *J. Mol. Biol.*, 296:1175-1181, 2000.
Lorbach et al., "Site-specific recombination in human cells catalyzed by phage λ integrase mutants," *J. Mol. Biol.*, 296:1175-1181, 2000.
Müller, "Ten years of gene targeting: targeted mouse mutants, from vector design to phenotype analysis," *Mech. Develop.*, 82:3-21, 1999.
Schwikardi et al., "Site-specific recombination in mammalian cells catalyzed by γδ resolvase mutants: implications for the topology of episomal DNA," *FEBS Letters*, 471:147-150, 2000.

*Primary Examiner*—Maria B Marvich
(74) *Attorney, Agent, or Firm*—Fulbright & Jaworski L.L.P.

(57) ABSTRACT

The present invention relates to a method of sequence-specific recombination of DNA in eukaryotic cells, comprising the introduction of a first DNA comprising a nucleotide sequence containing at least one recombination sequence into a cell, introducing a second DNA comprising a nucleotide sequence containing at least one further recombination sequence into a cell, and performing the sequence specific recombination by a bacteriophage lambda integrase Int.

21 Claims, 4 Drawing Sheets

SEQUENCE SPECIFIC DNA RECOMBINATION IN EUKARYOTIC CELLS

This application claims benefit of priority to U.S. Ser. No. 10/310,695, filed Dec. 5, 2002, and now U.S. Pat. No. 7,491,539. The entire contents of the foregoing application is hereby incorporated by reference.

BACKGROUND OF THE INVENTION

A. Field of the Invention

The present invention relates to a method of sequence-specific recombination of DNA in eukaryotic cells, comprising the introduction of a first DNA comprising a nucleotide sequence containing at least one recombination sequence into a cell, introducing a second DNA comprising a nucleotide sequence containing at least one further recombination sequence into a cell, and performing the sequence specific recombination by a bacteriophage lambda integrase Int.

B. Related Art

The controlled manipulation of eukaryotic genomes and the expression of recombinant proteins from episomal vectors are important methods for analyzing the function(s) of specific genes in living organisms. Moreover, said manipulations play a role in gene therapeutic methods in medicine. In this context the generation of transgenic animals, the change of genes or gene segments (so-called "gene targeting") and the targeted integration for foreign DNA into the genome of higher eukaryotes are of particular importance. Recently, these technologies could be improved by means of characterization and application of sequence specific recombination systems.

Furthermore, sequence-specific integration of expression cassettes, encoding and expressing a desired polypeptide/product, into the genome of biotechnological relevant host cells also gets more significance for the production of biopharmaceuticals. Expression level for a desired polypeptide in a stable transformed cell lines depends on the site of integration. By sequence specific integration, sites could be preferably used having a high transcription activity. The conventional method for generating production cell lines expressing a desired polypeptide/product is based on the random integration of the recombinant expression vector into the genome of the host cell. Variations in the expression level of the integrated gene(s) of interest in stable transformed cell lines are attributed mainly to differences in chromosomal locations and copy numbers. Random integration in the proximity of heterochromatin results in variable levels of transgene expression. Chromosome locations promoting the expression of the integrated gene(s) of interest are thought to be transcriptionally active regions of euchromatin. This randomness of integration causes a large diversity in recombinant cells robustness, productivity and quality, necessitating an elaborate screening process to identify and isolate a suitable cell clone producing the desired polypeptide at high level. In addition, the heterogeneity also means that for each clone an optimized production process has to be developed, making the development of a suitable production cell line a time consuming, labor intensive and costly process.

Conservative sequence specific DNA recombinases have been divided into two families. Members of the first family, the so-called "integrase" family, catalyze the cleavage and rejoining of DNA strands between two defined nucleotide sequences, which will be named as recombination sequences in the following. The recombination sequences may be either on two different or on one DNA molecule, resulting in inter- or intramolecular recombination, respectively. For intramolecular recombination, the result of the reaction depends on the respective orientation of the recombination sequences to each other. In the case of an inverted, i.e., opposite orientation of the recombination sequences, inversion of the DNA segments lying between the recombination sequences occurs. In the case of direct, i.e., tandem repeats of the recombination sequences on a DNA substrate, a deletion occurs. In case of the intermolecular recombination, i.e., if both recombination sequences are located on two different DNA molecules, a fusion of the two DNA molecules may occur. While members of the integrase family usually catalyze both intra- as well as intermolecular recombination, the recombinases of the second family of the so-called "invertases/resolvases" are only able to catalyze the intramolecular recombination.

At present, the recombinases which are used for the manipulation of eukaryotic genomes belong to the integrase family. Said recombinases are the Cre recombinase of the bacteriophage P1 and the Flp recombinase from yeast (Müller, 1999). The recombination sequences to which the Cre recombinase binds are named loxP. LoxP is a 34 bp long nucleotide sequence consisting of two 13 bp long inverted nucleotide sequences and an 8 bp long spacer lying between the inverted sequences (Hoess et al., 1985). The FRT named binding sequences for Flp are build up similarly. However, they differ from loxP (Kilby et al. 1993. Therefore, the recombination sequences may not be replaced by each other, i.e., Cre is not able to recombine FRT sequences and FLP is not able to recombine loxP sequences. Both recombination systems are active over long distances, i.e., the DNA segment to be inverted or deleted and flanked by two loxP or FRT sequences may be several 10 000 base pairs long.

For example, a tissue specific recombination in a mouse system, a chromosomal translocation in plants and animals, and a controlled induction of the gene expression was achieved with said two systems; review article of Müller, (1999). The DNA polymerase β was deleted in particular tissues of mice in this way; Gu et al. (1994). A further example is the specific activation of the DNA tumor virus SV40 oncogene in the mouse lenses leading to tumor formation exclusively in these tissues. The Cre-loxP strategy was used also in connection with inducible promotors. For example, the expression of the recombinase was regulated with an interferon-inducible promotor leading to the deletion of a specific gene in the liver and not—or only to a low extent—in other tissues; Kühn et al. (1995).

So far, three members of the invertase/resolvase family have been used for the manipulation of eukaryotic genomes. A mutant of the bacteriophage Mu invertase Gin can catalyze the inversion of a DNA fragment in plant protoplasts without cofactors. However, it has been discovered that this mutant is hyper-recombinogenic, i.e., it catalyzes DNA strand cleavages also at other than its naturally recombination sequences. This leads to unintended partially lethal recombination events in plant protoplast genomes. The β-recombinase from *Streptococcus pyogenes* catalyses the recombination in mouse cell cultures between two recombination sequences as direct repeats leading to the excision of the segment. However, simultaneously with deletion also inversion has been detected which renders the controlled use of the system for manipulation of eukaryotic genomes unsuitable. Mutants of the γδ resolvase from *E. coli* have been shown to be active on episomal and artificially introduced genomic recombination sequences, but the efficiency of the latter reaction is still rather poor.

The manipulation of eukaryotic genomes with the Cre and Flp recombinase, respectively, shows significant disadvantages. In case of deletion, i.e., the recombination of two tandem repeated loxP or FRT recombination sequences in a genome there is an irreversibly loss of the DNA segment lying between the tandem repeats. Thus, a gene located on this DNA segment will be lost permanently for the cell and the organism. Therefore, the reconstruction of the original state for a new analyses of the gene function, e.g., in a later developmental stage of the organism, is impossible. The irreversible loss of the DNA segment caused by deletion may be avoided by an inversion of the respective DNA segment. A gene may be inactivated by an inversion without being lost and may be switched on again at a later developmental stage or in the adult animal by means of a timely regulated expression of the recombinase via back recombination. However, the use of both Cre and Flp recombinases in this modified method has the disadvantage that the inversion cannot be regulated as the recombination sequences will not be altered as a result of the recombination event. Thus, repeated recombination events occur causing the inactivation of the respective gene due to the inversion of the respective DNA segment only in some, at best in 50% of the target cells at equilibrium of the reaction. There have been efforts to solve this problem, at least in part, by constructing mutated loxP sequences which cannot be used for further reaction after a single recombination. However, the disadvantage is the uniqueness of the reaction, i.e., there is no subsequent activation by back recombination after inactivation of the gene by inversion.

A further disadvantage of the Flp recombinase is its reduced heat stability at 37° C. thus limiting the efficiency of the recombination reaction in higher eukaryotes significantly, e.g., in mice with a body temperature of about 39° C. Therefore, Flp mutants have been generated which exhibit a higher heat stability as the wild-type recombinase. However, even these mutant Flp enzymes still exhibit a lower recombination efficiency than the Cre recombinase.

A further use of sequence specific recombinases resides in the medical field, e.g., in gene therapy, where the recombinases integrate a desired DNA segment into the genome of a respective human target cell in a stable and controlled way. Both Cre and Flp may catalyze intermolecular recombination. Both recombinases recombine a plasmid DNA which carries a copy of its respective recombination sequence with a corresponding recombination sequence which has been inserted before into the eukaryotic genome via homologous recombination. However, it is desirable that this reaction includes a "naturally" occurring recombination sequence in the eukaryotic genome. Because loxP and FRT are 34 and 54 nucleotides long, respectively, occurrence of exact matches of these recombination sequences as part of the genome is statistically unlikely. Even if a recombination sequence would be present, the disadvantage of the aforementioned back reaction still exists, i.e., both Cre and Flp recombinase may excise the inserted DNA segment after successful integration by intramolecular recombination.

Thus, one problem of the present invention is to provide a simple and controllable recombination system, and the required working means. A further problem of the present invention is the provision of a recombination system and the required working means, which may carry out a stable and targeted integration of a desired DNA sequence. A further problem of the present invention is the provision of methods which allows the generation of an improved protein expression system on the basis of one of those recombination systems.

SUMMARY OF THE INVENTION

Thus, in accordance with the present invention, there is provided a method of promoting sequence specific recombination of DNA in a eukaryotic cell comprising (a) providing a eukaryotic cell comprising a DNA comprising a first attB, attP, attL or attR sequence, or a derivative thereof; (b) introducing into the cell a DNA comprising a second attB, attP, attL or attR sequence, or a derivative thereof, into a cell, wherein if said first DNA comprises an attB sequence, or a derivative thereof, said second DNA comprises an attB, attL or attR sequence, or a derivative thereof, or wherein if said first DNA comprises an attP sequence, or a derivative thereof, said second DNA comprises an attP, attL or attR sequence, or a derivative thereof, or wherein if said first DNA comprises an attL sequence, or a derivative thereof, said second DNA comprises an attB, attP or attL sequence, or a derivative thereof, or wherein if said first DNA comprises an attR sequence, or a derivative thereof, said second DNA comprises an attB, attP or attR sequence, or a derivative thereof; and (c) providing to the cell a bacteriophage lambda integrase Int under conditions that support integrase-mediated sequence specific recombination. The first att sequence, or a derivative thereof, is integrated in an artificial-/minichromosome or the genome of said cell. The first att sequence, or a derivative thereof, may naturally occur in the genome of said cell or be introduced into said cell.

In another embodiment, there is provided a method of producing a desired polypeptide in a eukaryotic cell comprising (a) providing a eukaryotic cell comprising a first DNA comprising an attB, attP, attL or attR sequence or a derivative thereof; (b) introducing a second DNA comprising an attB, attP, attL or attR sequence or a derivative thereof, and a segment encoding the polypeptide of interest into the cell; (c) contacting said cell with a bacteriophage lambda integrase Int under conditions supporting sequence-specific integrase-mediated recombination, wherein the second DNA is integrated into the first DNA; and (d) cultivating said cell under conditions, wherein the polypeptide of interest is produced. If said first DNA comprises an attB sequence, or a derivative thereof, said second DNA may comprise an attB, attL or attR sequence, or a derivative thereof, or wherein if said first DNA comprises an attP sequence, or a derivative thereof, said second DNA may comprise an attP, attL or attR sequence, or a derivative thereof, or wherein if said first DNA comprises an attL sequence, or a derivative thereof, said second DNA may comprise an attB, attP or attL sequence, or a derivative thereof, or wherein if said first DNA comprises an attR sequence, or a derivative thereof, said second DNA may comprise an attB, attP or attR sequence, or a derivative thereof. The first DNA may be integrated into the genome of the cell, an artificial-/minichromosome in the cell or an episomal element in the cell, before said second DNA is introduced into said cell.

In yet another embodiment, there is provided a method of producing a polypeptide of interest in a eukaryotic cell, said cell having at least one naturally-occurring recombination sequence which allows sequence-specific recombination mediated by an bacteriophage lambda Int, or a functional mutant thereof, comprising (a) introducing a DNA comprising an attB, attP, attL or attR sequence or a derivative thereof, and a segment encoding the polypeptide of interest into said cell; (b) contacting said cell with a bacteriophage lambda integrase Int under conditions supporting sequence-specific recombination by a bacteriophage lambda integrase Int between the recombination sequence naturally-occurring in said cell and the DNA introduced into said cell; and (c)

cultivating said cell under conditions, wherein the polypeptide of interest is produced. The naturally-occurring sequence may be attH. The desired polypeptide may be isolated from the host cell or the cell culture medium.

In accordance with the methods of the invention, the derivative of the attP, attB, attL or attR sequence may comprise one or more copies of the arm-binding site(s) for Int, or one or more copies of the core Int binding site(s), or a combination of one or more copies of the arm-binding site(s) for Int and one or more copies of the core Int binding site(s). The derivative of the attP, attB, attL or attR sequence may comprise one or more copies of the core Int binding site(s), or a combination of one or more copies of the arm-binding site(s) for Int and one or more copies of the core Int binding site(s). The core binding site may comprise nine contiguous base pairs and relates to DNA sequences consisting for the B-sequence of the nucleotide sequence 5'-CTGCTTTTT-3' (SEQ ID NO:18), for the B'-sequence of the nucleotide sequence 5'-CAAGTTAGT-3' (SEQ ID NO:19) (reverse complementary strand), for the C-sequence of the nucleotide sequence 5'-CAGCTTTTT-3' (SEQ ID NO:20), and for the C'-sequence of the nucleotide sequence 5'-CAACTTAGT-3' (SEQ ID NO:21) (reverse complementary strand) in wild-type att sites or said sequences having functional nucleotide substitutions.

In further accordance with the methods of the invention, sequence-specific recombination may be performed by Int, optionally with one or more cofactors selected from XIS, FIS and/or IHF. The Int may be a modified Int, such as Int-h or Int-h/218. The Int, XIS, FIS and/or IHF may be added to the cell in purified form or are co-expressed by said cell. The methods may comprise additional (second, third, fourth, etc.) DNA encoding an Int and/or one or more cofactors selected from XIS, FIS and/or IHF which is/are introduced into the cell.

The polypeptide of interest may be an antibody, hormone or growth factor. The eukaryotic cell may be a mammalian cell, such as a rodent cell, such as a mouse or a hamster cell. The hamster cell may be a BHK or CHO cell, and the mouse cell may be a murine myeloma cell, such as an NS0 or Sp2/0 cell.

BRIEF DESCRIPTION OF THE DRAWINGS

The invention is explained in more detail with the following illustrations:

(FIG. 2A) Intramolecular integrative (attB×attP) recombination. (FIG. 2B) Intermolecular integrative (attB×attP) recombination. (FIG. 2C) Intramolecular excisive (attL×attR) recombination. (FIG. 2D) Intermolecular excisive (attL×attR) recombination. Substrate vectors and expected recombination products are schematized at the top of each panel. The fraction of GFP-expressing cells was determined by FACS at three time points after co-transfection of substrate and expression vectors. We show mean values of three assays with standard deviations indicated by vertical lines.

(FIG. 3A) Pairs of substrate vectors for intermolecular recombination contain either attB or attP in different combinations and yield products that express GFP driven by the CMV promoter. (FIG. 3B) Various combinations of substrate vectors were co-transfected with expression vectors for wild-type Int, mutant Int-h, or Int-h/218. At 48 hrs, cells were analyzed by FACS and the ratio of GFP-expressing cells was determined for two pairs of substrates. Recombination between attP and attP served as reference, as indicated. Mean values of three assays with standard deviations indicated by vertical lines are shown. The actual mean values of GFP-expression cells (%) for Int were 0.08 (B×B), 1.24 (P×P), and 0.81 (P×B). Those for Int-h were 1.15 (B×B), 8.07 (P×P), and 9.90 (P×B). Those for Int-h/218 were 4.01 (B×B), 17.62 (P×P), and 16.45 (P×B).

(FIG. 4A) Schematic representation of substrate vectors which were incubated with or without IHF before transfection into HeLa cells that transiently expressed either wild-type Int or Int-h. (FIG. 4B) At 48 hrs after transfection, the fractions of GFP-expressing cells were analyzed by FACS. The ratio of these fractions was plotted as activation of recombination by IHF. The graph shows mean values of three assays with standard deviations indicated by vertical lines. The actual mean values of GFP-expressing cells (%) in the presence and absence of IHF, respectively, were for Int (7.93/1.26) and Int-h (17.57/13.14) in the case of intramolecular recombination, and for Int (13.94/3.47) and Int-h (20.33/16.83) analyzing intermolecular recombination.

DETAILED DESCRIPTION OF THE INVENTION

Definitions

Figure 1:
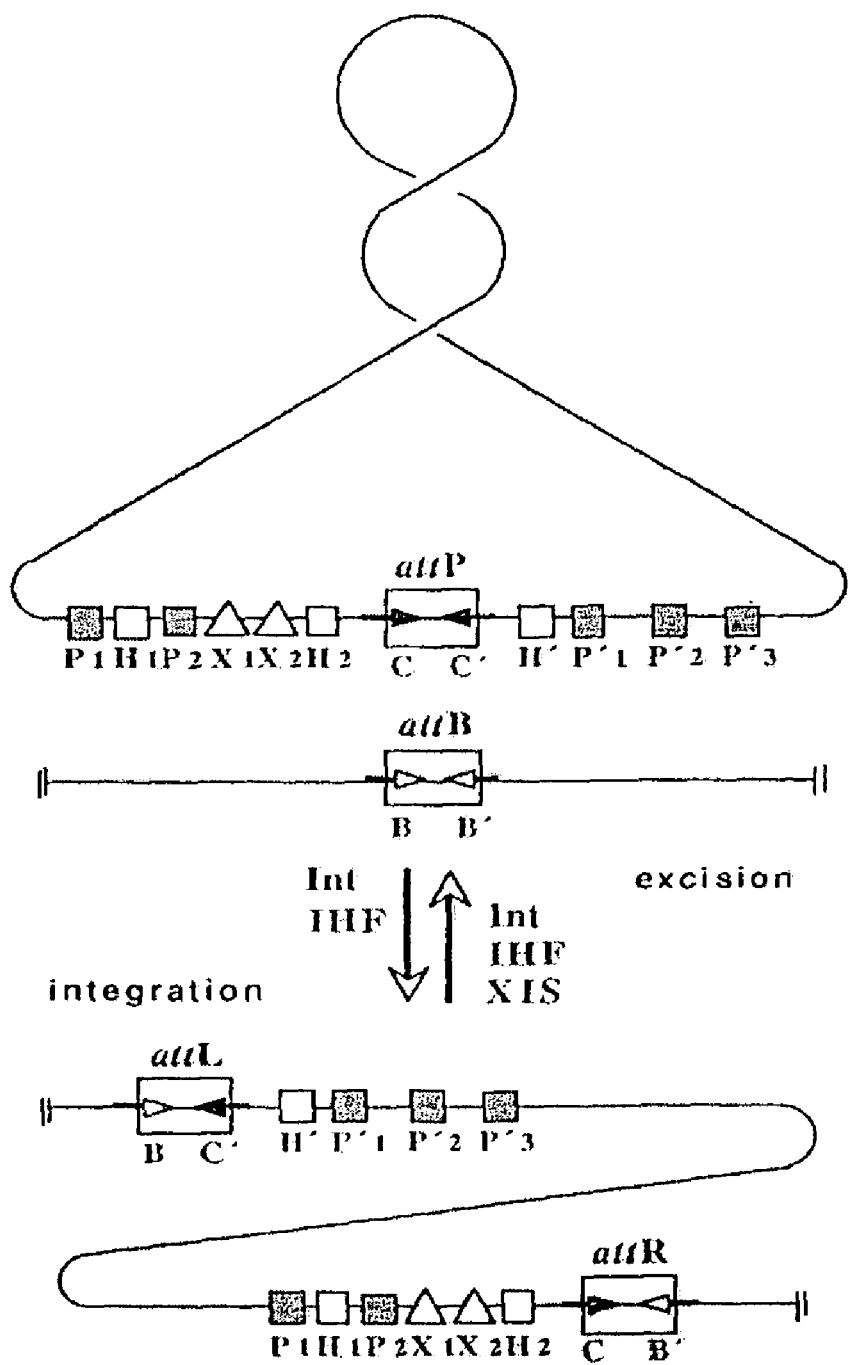
FIG. 1 shows a schematic presentation of the recombination reactions namely integration and excision catalyzed by the wild-type integrase Int. A superhelical plasmid DNA (top) carrying a copy of the recombination sequence attP is shown. AttP consists of five so-called arm binding sites for Int (P1, P2, P1', P2', P3'), two core Int binding sites (C and C'; marked with black arrows), three binding sites for IHF (H1, H2, H'), two binding sites for Xis (X1, X2) and the so-called overlap region (open rectangle) where the actual DNA strand exchange takes place. The natural partner sequence for attP, attB, is shown on a linear DNA segment beneath and consists of two core binding sites for Int (B and B'; marked with open arrows) and the overlap region. For the recombination between attB and attP, Int and IHF are necessary leading to the integration of the plasmid into the DNA segment carrying attB. Thereby, two new hybrid recombination sequences, attL and attR, are formed which serve as target sequences for the excision. The latter reaction requires in the wild-type situation Int and IHF, and a further cofactor XIS encoded by the phage lambda.

The term "transformation" or "to transform," "transfection" or "to transfect" as used herein means any introduction of a nucleic acid sequence into a cell, resulting in genetically modified, recombinant, transformed or transgenic cells. The introduction can be performed by any method well known in the art and described, e.g., in Sambrook et al. (1989) or Ausubel et al. (1994). Methods include but are not limited to lipofection, electroporation, polycation (such as DEAE-dextran)-mediated transfection, protoplast fusion, viral infections and microinjection or may be carried out by means of the calcium method, electroshock method, intravenous/intramusuclar injection, aerosol inhalation or an oocyte injection. The transformation may result in a transient or stable transformation of the host cells. The term "transformation" or "to transform" also means the introduction of a viral nucleic acid sequence in a way which is for the respective virus the naturally one. The viral nucleic acid sequence needs not to be present as a naked nucleic acid sequence but may be packaged in a viral protein envelope. Thus, the term relates not only to the method which is usually known under the term "transformation" or "to transform". Transfection methods that provide optimal transfection frequency and expression of the introduced nucleic acid are favored. Suitable methods can be determined by routine procedures. For stable transfectants the constructs are either integrated into the host cell's genome or an artificial chromosome/mini-chromosome or located episomally so as to be stably maintained within the host cell.

The term "recombination sequences" as used herein relates to attB, attP, attL and attR sequences and the derivatives thereof. An example for an attB sequence is specified in SEQ ID NO:13, an example for an attP sequence is specified in SEQ ID NO:14, an example for an attL sequence is specified in SEQ ID NO:15, and an example for an attR sequence is specified in SEQ ID NO:16.

The term "derivative" as used herein relates to attB, attP, attL and attR sequences having one or more substitutions, preferably seven, more preferably two, three, four, five or six in the overlap region and/or core region in contrast to naturally occurring attB, attP, attL and attR sequences. The term "derivative" also relates to at least one core Int binding site of attB, attP, attL or attR. The term "derivative" also relates to at least one core Int binding site of attP, attL or attR plus one or more copies of the arm-binding sites for Int. The term "derivative" also relates to at least one core Int binding site of attP, attL or attR plus one or more copies of the IHF, FIS or XIS factor binding sites. The term "derivative" also relates to a combination of these features. The term "derivative" moreover relates to any functional fragments thereof and to endogenous nucleotide sequences in eukaryotic cells supporting sequence-specific recombination, e.g. attH identified in the human genome (see e.g. WO 01/16345). The term "derivative" in general includes attB, attP, attL or attR sequences suitable for realizing the intended use of the present invention, which means that the sequences mediate sequence-specific recombinantion events driven by an integrase (wild-type or modified) of the bacteriophage lambda.

The term "functional fragment" relates to attB, attP, attL and attR sequences having substitutions, deletions, and/or insertions (including presence or absence of wild-type or modified protein binding sites), which do not significantly affect the use of said sequences in recombination events driven by an wild-type or modified integrase of the bacteriophage lambda. Functionality is not significantly affected, when recombination frequency is at least about 70%, preferably at least about 80%, more preferably about 90%, further more preferably at least about 95%, and most preferably more than about 100% in comparison to the corresponding naturally occurring recombination sequences, using the same recombinase under the same conditions (e.g., in vitro or in vivo use, identical host cell type, identical transfection conditions, presence or absence of the same host factors, the same buffer conditions, identical temperature, etc.). Alternatively, substitutions, deletions, and/or insertions in attB, attP, attL and/or attR sequences confer at least an enhancement of the recombination events driven by a wild-type or modified integrase of the bacteriophage lambda, whereby said enhancement may consist for example of (i) increasing the efficiency of recombination events (integration and/or excision), (ii) increasing the specificity of recombination, (iii) favoring excisive recombination events, (iv) favoring integrative recombination events, (v) relieving the requirements for some or all host factors, in comparison to the corresponding naturally occurring recombination sequences using the same recombinase under the same conditions (see above).

The functionality of modified recombination sites or of modified integrase can be demonstrated in ways that depend on the desired particular characteristic and are known in the art. For example, a co-transfection assay as described in the present invention (see Results 5.1 or Example 3 of WO 01/16345) may be used to characterize integrase-mediated recombination of extrachromosomal DNA in a variety of cell lines. Briefly, cells are co-transfected with an expression vector encoding the integrase protein and a substrate vector that is a substrate for the recombinase, encoding a functional/non-functional reporter gene (e.g., fluorescent protein like GFP) and containing at least one recombination sequence therein. Upon expression of the integrase by the expression vector, the function of the reporter gene will be rendered non-functional/functional. Thus, the recombination activity can be assayed either by recovering the recombined substrate vector and looking for evidence of recombination at the DNA level (for example by performing a PCR, sequence analysis of the recombined region, restriction enzyme analysis, Southern blot analysis) or by looking for evidence of the recombination at the protein level (e.g., ELISA, Western Blotting, radioimmunoassay, immunoprecipitation, immunostaining, FACS-analysis of fluorescent proteins).

The term "overlap region" as used herein defines the sequence of the recombination sequences where the DNA strand exchange, including strand cleavage and religation, takes place and relates to the consensus DNA sequence 5'-TT-TATAC-3' (SEQ ID NO:22) in wild-type att sites or said sequence having functional nucleotide substitutions. The only prerequisite is, that the sequence of the overlap region is identical between recombining partner sequences.

The term "core binding sites" relates to two imperfectly repeated copies in inverted orientation, separated by the overlap region, in each set of wild-type att sites. The core binding sites are essential for the recombination by binding the integrase at low affinity. Each core binding site consists of nine contiguous base pairs and relates to DNA sequences consisting for the B-sequence of the nucleotide sequence 5'-CTGCTTTTT-3', for the B'-sequence of the nucleotide sequence 5'-CAAGTTAGT-3' (reverse complementary strand), for the C-sequence of the nucleotide sequence 5'-CAGCTTTTT-3', and for the C'-sequence of the nucleotide sequence 5'-CAACTTAGT-3' (reverse complementary strand) in wild-type att sites or said sequences having functional nucleotide substitutions.

The term "arm-binding site for Int" or "arm-binding sites" as used herein relates to the consensus sequence 5'-C/AAGT-CACTAT-3' (SEQ ID NO:1) or said sequence having functional nucleotide substitutions. The arm-binding site for Int may be positioned at various distances upstream and/or downstream of the core Int binding site(s).

The term "homologue" or "homologous" or "similar" as used herein with regard to recombination sequences, arm-binding sites, and host factor binding sites relates to a nucleic acid sequence being identical for about 70%, preferably for about 80%, more preferably for about 85%, further more preferably for about 90%, further more preferably for about 95%, and most preferably for about 99% to naturally occurring recombination sequences, arm-binding sites, and host factor binding sites. As homologous or similar are considered sequences, using standard parameters in the similarity algorithm BLAST of NCBI (Basic Local Alignment Search Tool, Altschul et al., (1990)) show a probability of $P<10^{-5}$ when compared to the recombination sequences.

The term "vector" as used herein relates to naturally occurring or synthetically generated constructs for uptake, proliferation, expression or transmission of nucleic acids in a cell, e.g., plasmids, phagemids, cosmids, artificial chromosomes/mini-chromosomes, bacteriophages, viruses or retro viruses. Methods used to construct vectors are well known to a person skilled in the art and described in various publications. In particular techniques for constructing suitable vectors, including a description of the functional and regulatory components such as promoters, enhancers, termination and polyadenylation signals, selection markers, origins of replication, and splicing signals, are reviewed in considerable details in Sambrook et al. (1989), supra, and references cited therein. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif.

The terms "gene of interest", "desired sequence," or "desired gene" as used herein have the same meaning and refer to a polynucleotide sequence of any length that encodes a product of interest. The selected sequence can be full length or a truncated gene, a fusion or tagged gene, and can be a cDNA, a genomic DNA, or a DNA fragment, preferably, a cDNA. It can be the native sequence, i.e., naturally occurring form(s), or can be mutated or otherwise modified as desired. These modifications include codon optimizations to optimize codon usage in the selected host cell, humanization or tagging. The selected sequence can encode a secreted, cytoplasmic, nuclear, membrane bound or cell surface polypeptide. The "product of interest" includes proteins, polypeptides, fragments thereof, peptides, antisense RNA all of which can be produced in the selected host cell.

The term "nucleic acid sequence", "nucleotide sequence", or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The polynucleotides of the invention include nucleic acid regions wherein one or more codons have been replaced by their synonyms.

The nucleic acid sequences of the present invention can be prepared using standard techniques well known to one of skill in the art. The term "encoding" or "coding" refers to the inherent property of specific sequences of nucleotides in a nucleic acid, such as a gene in chromosome or an mRNA, to serve as templates for synthesis of other polymers and macromolecules in biological processes having a defined sequence of nucleotides (i.e., rRNA, tRNA, other RNA molecules) or amino acids and the biological properties resulting therefrom. Thus a gene encodes a protein, if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for the transcription, of a gene or cDNA can be referred to as encoding the protein or other product of that gene or cDNA. A nucleic acid that encodes a protein includes any nucleic acids that have different nucleotide sequences but encode the same amino acid sequence of the protein due to the degeneracy of the genetic code. Nucleic acids and nucleotide sequences that encode proteins may include introns.

The term "polypeptide" is used interchangeably with amino acid residue sequences or protein and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties. Amino acid modifications can be prepared for example by performing site-specific mutagenesis or polymerase chain reaction mediated mutagenesis on its underlying nucleic acid sequence.

The term "expressed" as used herein refers to transcription and/or translation of a heterologous nucleic acid sequence within a host cell. "Production" would involve both transcription and translation. The level of expression in a host cell may be determined on the basis of either the amount of corresponding mRNA that is present in the cell, and production would be based on the amount of the desired polypeptide. For example, mRNA transcribed from a selected sequence can be quantitated by Northern blot hybridization, ribonuclease RNA protection, in situ hybridization to cellular RNA or by PCR (see Sambrook et al. (1989), supra; Ausubel et al. (1994 updated), supra). Proteins encoded by a selected sequence can be quantitated by various methods, e.g., by ELISA, by Western blotting, by radioimmunoassays, by immunoprecipitation, by assaying for the biological activity of the protein, or by immunostaining of the protein followed by FACS analysis PCR (see Sambrook et al. (1989), supra; Ausubel et al. (1994 updated), supra).

An "expression cassette" defines a region within a construct that contains one or more genes to be transcribed, wherein the genes contained within the segment are operatively linked to each other and transcribed from a single promoter, and as result, the different genes are at least transcriptionally linked. More than one protein or product can be transcribed and translated from each transcription unit. Each transcription unit will comprise the regulatory elements necessary for the transcription and translation of any of the selected sequence that are contained within the unit.

The term "operatively linked" means that two or more nucleic acid sequences or sequence elements are positioned in a way that permits them to function in their intended manner. For example, a promoter and/or enhancer is operatively linked to a coding sequence if it acts in cis to control or modulate the transcription of the linked sequence. Generally, but not necessarily, the DNA sequences that are operatively linked are contiguous and, where necessary to join two protein coding regions or in the case of a secretory leader, contiguous and in reading frame.

The term "selection marker gene" refers to a gene that only allows cells carrying the gene to be specifically selected for or against in the presence of a corresponding selection agent. By way of illustration, an antibiotic resistance gene can be used as a positive selectable marker gene that allows the host cell transformed with the gene to be positively selected for in the presence of the corresponding antibiotic; a non-transformed host cell would not be capable of growth or survival under the selection culture conditions. Selectable markers can be positive, negative or bifunctional. Positive selectable markers allow selection for cells carrying the marker by conferring resistance to a drug or compensate for a metabolic or catabolic defect in the host cell. In contrast, negative selection markers allow cells carrying the marker to be selectively eliminated. For example, using the HSV-tk gene as a marker will make the cells sensitive to agents such as acyclovir and gancyclovir. The selectable marker genes used herein, including the amplifiable selectable genes, will include recombinantly engineered mutants and variants, fragments, functional equivalents, derivatives, homologs and fusions of the native selectable marker gene so long as the encoded product retains the selectable property. Useful derivatives generally have substantial sequence similarity (at the amino acid level) in regions or domains of the selectable marker associated with the selectable property. A variety of marker genes have been described, including bifunctional (i.e., positive/negative) markers (see e.g., WO 92/08796 and WO 94/28143), incorporated by reference herein. For example, selectable genes commonly used with eukaryotic cells include the genes for aminoglycoside phosphotransferase (APH), hygromycin phosphotransferase (HYG), dihydrofolate reductase (DHFR), thymidine kinase (TK), glutamine synthetase, asparagine synthetase, and genes encoding resistance to neomycin (G418), puromycin, histidinol D, bleomycin and phleomycin.

Selection may also be made by fluorescence activated cell sorting (FACS) using for example a cell surface marker, bacterial P-galactosidase or fluorescent proteins (e.g., green fluorescent proteins (GFP) and their variants from *Aequorea victoria* and *Renilla reniformis* or other species; red fluorescent proteins, fluorescent proteins and their variants from non-bioluminescent species (e.g., *Discosoma* sp., *Anemonia* sp., *Clavularia* sp., *Zoanthus* sp.) to select for recombinant cells.

The term "selection agent" refers to a substance that interferes with the growth or survival of a host cell that is deficient in a particular selectable gene. For example, to select for the presence of an antibiotic resistance gene like APH (aminoglycoside phosphotransferase) in a transfected cell the antibiotic Geneticin (G418) is used.

Integrases

The integrase (usually and designated herein as "Int") of the bacteriophage lambda belongs like Cre and Flp to the integrase family of the sequence specific conservative DNA recombinases. In its natural function Int catalyses the integrative recombination between two different recombination sequences namely attB and attP. AttB comprises 21 nucleotides and was originally isolated from the *E. coli* genome; Mizuuchi and Mizuuchi (1980). On the other hand attP having 243 nucleotides is much longer and occurs naturally in the genome of the bacteriophage lambda; Landy and Ross (1977. The Int recombinase has seven binding sites altogether in attP and two in attB. The biological function of Int is the sequence specific integration of the circular phage genome into the locus attB on the *E. coli* chromosome. Int needs a protein co-factor, the so-called integration host factor (usually and designated herein as "IHF") for the integrative recombination; Kikuchi and Nash (1978). IHF is needed for the assembly of a functional recombination complex with attP. A second co-factor for the integration reaction is the DNA negative supercoiling of attP. Finally, the recombination between attB and attP leads to the formation of two new recombination sequences, namely attL and attR, which serve as substrate and recognition sequence for a further recombination reaction, the excision reaction. A comprehensive summary of the bacteriophage lambda integration is given, e.g., in Landy (1989).

The excision of the phage genome out of the bacterial genome is catalyzed by the Int recombinase also. For this, a further co-factor is needed in addition to Int and IHF, which is encoded by the bacteriophage lambda. This is the excisionase (usually and designated herein as "XIS") having two binding sites in attR; Gottesman and Weisberg (1971). In contrast to the integrative recombination, DNA negative supercoiling of the recombination sequences is not necessary for the excisive recombination. However, DNA negative supercoiling increases the efficiency of the recombination reaction. A further improvement of the efficiency of the excision reaction may be achieved with a second co-factor namely FIS (factor for inversion stimulation), which acts in conjunction with XIS; Landy (1989). The excision is genetically the exact reverse reaction of the integration, i.e., attB and attP are generated again. A comprehensive summary of the bacteriophage lambda excision is given, e.g., in Landy (1989).

The Present Invention

One aspect of the present invention relates to a method of sequence specific recombination of DNA in a eukaryotic cell, comprising:
 a) introducing a first attB, attP, attL or attR sequence or a derivative thereof into a cell,
 b) introducing a second attB, attP, attL or attR sequence or a derivative thereof into a cell, wherein if said first DNA sequence comprises an attB sequence or a derivative thereof said second sequence comprises an attB, attL or attR sequence or a derivative thereof, or wherein if said first DNA sequence comprises an attP sequence or a derivative thereof said second sequence comprises an attP, attL or attR sequence or a derivative thereof, or wherein if said first DNA sequence comprises an attL sequence or a derivative thereof said second sequence comprises an attB, attP or attL sequence or a derivative thereof, or wherein if said first DNA sequence comprises an attR sequence or a derivative thereof said second sequence comprises an attB, attP or attR sequence or a derivative thereof,
 c) performing the sequence-specific recombination by a bacteriophage lambda integrase Int.

Preferred is the method wherein in step c) the sequence-specific recombination is performed by Int or by Int and XIS, FIS, and/or IHF. Most preferred is the method wherein in step c) the sequence-specific recombination is performed by Int or by Int and a XIS factor, or by Int and IHF, or by Int and XIS and IHF. Further preferred is the method wherein in step c) the sequence-specific recombination is performed by a modified Int, preferably the Int-h or Int-h/218. In this context, use of a modified Int together with XIS, FIS and/or IHF is also within the meaning of the present invention.

In a more preferred embodiment of this method, sequence specific recombination of DNA in a eukaryotic cells will be performed between identically or nearly identically recombination sites. Therefore, the present invention relates a method of sequence specific recombination as described above, wherein if said first DNA sequence comprises an attB sequence or a derivative thereof said second sequence comprises also attB sequence or a derivative thereof, or wherein if said first DNA sequence comprises an attP sequence or a derivative thereof said second sequence comprises an attP sequence or a derivative thereof, or wherein if said first DNA sequence comprises an attL sequence or a derivative thereof said second sequence comprises an attL sequence or a derivative thereof, or wherein if said first DNA sequence comprises an attR sequence or a derivative thereof said second sequence comprises an attR sequence or a derivative thereof.

The method of the present invention may be carried out not only with the naturally occuring attB, attP, attL, and/or attR sequences but also with modified, e.g., substituted attB, attP, attL, and/or attR sequences. For example an integrative recombination of the bacteriophage lambda and *E. coli* between attP and attB homologous sequences (mutants of the wild-type sequences) have been observed which have one or more substitutions in attB (Nash, 1981; Nussinov. and Weisberg, 1986 and/or in attP (Nash, 1981).

Thus, the present invention relates to a method wherein the used attB, attP, attL, and/or attR sequences have one or more substitutions in comparison to the naturally occuring attB, attP, attL, and/or attR sequences. Preferred is a method wherein the attB, attP, attL, and/or attR sequences have one, two, three, four, five, six, seven or more substitutions. The substitutions may occur both in the overlap region and in the core region. The complete overlap region comprising seven nucleotides may be substituted also. More preferred is a method wherein substitutions are introduced into the attB, attP, attL, and/or attR sequences either in the core region or in the overlap region. Preferred is the introduction of a substitution in the overlap region and the simultaneous introduction of one or two substitutions in the core region. The present invention also relates to a method wherein the used attB, attP, attL, and/or attR sequences are derivatives, including functional fragments thereof, of said recombination sites in comparison to the naturally occurring attB, attP, attL, and/or attR sequences.

A modification in the form of one or more substitution(s) into recombination sequences is to be chosen such that the recombination can be carried out in spite of the modification(s). Examples for such substitutions are listed e.g., in the publications of Nash (1981), supra and Nussinov and Weisberg (1986), supra and are not considered to be limiting. Further modifications may be easily introduced, e.g., by mutagenesis methods (a number of these are described in Ausubel et al. (1994 updated), supra) and and may be tested for their use by test recombinations as described, e.g., in the examples of the present invention (Examples 1 and 2, results 5.1).

Furthermore, the present invention relates to a method wherein the used attB, attP, attL, and/or attR sequences comprise only of one of the respective core Int binding sites, however, more than two core Int binding sites are also preferred. In a preferred embodiment, the present invention relates to a method wherein the used attB, attP, attL, and/or attR sequences consist only of one of the respective core Int binding sites. In a further embodiment the used attB, attP, attL, and/or attR sequences consist of two or more core Int binding sites.

The present invention relates further to a method wherein the used attP, attL, and/or attR sequences comprise in addition to the core Int binding site one or more, preferably two, three, four, five or more than five, copies of the arm-binding site for Int. Said binding site comprises a consensus motive having the sequence 5'-C/AAGTCACTAT-3' (SEQ ID NO:1) or a modified sequence thereof having nucleotide substitutions and being functional with regard to the Int binding. The arm-binding site(s) for Int may be positioned at various distances upstream and/or downstream of the core Int binding site(s).

In order to perform the method of the present invention the first recombination sequence may comprise further DNA sequences which allow the integration into a desired target locus, e.g., in the genome of the eukaryotic cell or an artificial-/minichromosome. This recombination occurs, e.g., via the homologous recombination which is mediated by internal cellular recombination mechanisms. For said recombination, the further DNA sequences have to be homologous to the DNA of the target locus and located both 3' and 5' of the attB, attL, attP, or attR sequences or derivatives thereof, respectively. The person skilled in the art knows how great the degree of the homology and how long the respective 3' and 5' sequences have to be such that the homologous recombination occurs with a sufficient probability; see review of Capecchi (1989).

However, it is also possible to integrate the first recombination sequence by any other mechanism into the genome of the eukaryotic cell, or any artificial-/minichromosome, e.g., via random integration which is also mediated by internal cellular recombination events. Integration of said first recombination site via sequence-specific recombination using sites different from those being integrated, e.g., by using loxP/FRT sequences, is also conceivable.

The second recombination sequence may also comprise DNA sequences which are necessary for an integration into a desired target locus via homologous recombination. For the method of the present invention both the first and/or the second recombination sequence may comprise the further DNA sequences. Preferred is a method wherein both DNA sequences comprise the further DNA sequences.

Introduction of the first and second recombination sequence with or without further DNA sequences may be performed both consecutively and in a co-transformation wherein the recombination sequences are present on two different DNA molecules. Preferred is a method, wherein the first and second recombination sequence with or without further DNA sequences are present and introduced into the eukaryotic cells on a single DNA molecule. Furthermore, the first recombination sequence may be introduced into a cell and the second recombination sequence may be introduced into another cell wherein the cells are fused subsequently. The term fusion means crossing of organisms as well as cell fusion in the widest sense.

The method of the present invention may be used, e.g., to invert a DNA segment lying between the indirectly orientated recombination sequences in an intramolecular recombination. Furthermore, the method of the present invention may be used to delete the DNA segment lying between the directly orientated recombination sequences in an intramolecular recombination. If the recombination sequences are each incorporated in 5'-3' or in 3'-5' orientation they are present in direct orientation. The recombination sequences are in indirect orientation if, e.g., the attB sequence is integrated in 5'-3' and the attP sequence is integrated in 3'-5' orientation. If the recombination sequences are each incorporated, e.g., via homologous recombination into intron sequences 5' and 3' of an exon and the recombination is performed by an integrase, the exon would be inverted in case of indirectly orientated recombination sequences and deleted in case of directly orientated recombination sequences, respectively. With this procedure the polypeptide encoded by the respective gene may lose its activity or function or the transcription may be stopped by the inversion or deletion such that no (complete) transcript is generated. In this way, e.g., the biological function of the encoded polypeptide may be investigated. Moreover, inversion or deletion reactions may be used to activate the expression of a gene encoding a desired polypeptide, e.g., by functional linkage of the open reading frame of the encoded polypeptide with regulatory elements which allow transcription and/or translation of the encoded polypeptide. Those regulatory elements include but are not limited to a promotor and or promotor/enhancer elements, which are well known in the art for various eukaryotic expression systems.

However, the first and/or second recombination sequence may comprise further nucleic acid sequences encoding one or more polypeptides/products of interest. For example a structural protein, an enzymatic or a regulatory protein may be introduced via the recombination sequences into the genome being transiently or stably expressed after intramolecular recombination. The introduced polypeptide/product may be an endogenous or exogenous one. Furthermore, a marker protein or biopharmaceutically relevant therapeutic polypeptides may be introduced. The person skilled in the art knows that this listing of applications of the method according to the present invention is only exemplary and not limiting. Examples of applications according to the present invention performed with the so far used Cre and Flp recombinases may be found, e.g. in the review of Kilby et al. (1993).

Furthermore, the method of the present invention may be used to delete or invert DNA segments on vectors by an intramolecular recombination on episomal substrates. A deletion reaction may be used, e.g., to delete packaging sequences from so-called helper viruses. This method has a broad application in the industrial production of viral vectors for gene therapeutic applications; Hardy et al. (1997).

The intermolecular recombination leads to the fusion of two DNA molecules each having a copy of attB, attP, attL, or attR or various combinations of att sequences or of their derivates. For example, attB or a derivative thereof may be introduced first via homologous recombination in a known, well characterized genomic locus of a cell or an artificial-/minchromosome. Subsequently an attB, attP, attL, or attR carrying vector or DNA-segment may be integrated into said genomic attB sequence via intermolecular recombination. Preferred in this method is the co-expression of the mutant integrase, e.g., Int-h or Int-h/218 within the eukaryotic cell, wherein the recombination occurs. Most preferred is the co-expression of the mutant integrase Int-h/218. Genes encoding for any of those mutant integrases may be located on a second DNA vector being transfected, preferably co-transfected, or on the vector or DNA-segment carrying the attP, attL, attR or also an attB sequence or an derivative thereof. Further sequences may be located on the attB, attP, attL, or attR carrying vector or DNA-segment, e.g., a gene for a particular marker protein flanked by loxP/FRT sequences. With this approach it may be achieved that, e.g., in comparative expression analyses of different genes in a cell type, said genes are not influenced by positive or negative influences of the respective genomic integration locus. Furthermore, the method of the present invention may be used to fuse DNA segments on vectors by an intermolecular recombination on episomal substrates. A fusion reaction may be used, e.g., to produce recombinant proteins or relevant domains in order to screen for phenotypes. This method may be used in the high throughput analysis of protein functions in eukaryotic cells and is thus of considerable interest.

As mentioned above, intermolecular recombination may be used to introduce one or more gene(s) of interest encoding one or more desired polypeptide(s)/product(s) into, e.g., episomal substrates, artificial-/minichromosomes, or various host cell genomes containing a first recombination sequence. In this context a second DNA comprises beside at least one recombination sequence, e.g., attP, attB, attL, attR or any derivative thereof, one or more expression cassette(s) for the production of one or more desired protein(s)/product(s). That expression cassette may be introduced into a desired target locus via the recombination sequences which allows sequence-specific recombination between the DNA comprising the second recombination sequence and the expression cassette, and the first recombination sequence being introduced before into said episomal substrate, artificial-/minichromosome, or host cell genome. This embodiment may be of high interest for establishing high expression cell lines which are suitable for the production of biopharmaceutical products.

In this context, a first DNA comprising at least one recombination sequence has to be introduced, e.g., by random integration, into the genome of the host cell, an artificial-/minichromosomes or episomal substrates contained within the host cell. Alternatively, host cell may be transformed with an artificial-/minichromosome or episomal substrate comprising a corresponding at least one recombination site(s). Another way to integrate recombination sequence(s) into a desired target locus, recognized by a bacteriophage lambda integrase Int, is to use homologous recombination techniques as mentioned above.

To facilitate selection for stable transfectants which have introduced recombination sequence(s) into a desired target locus, a selection marker gene is co-introduced into the same target locus at the same time. This may be achieved, for example, if the recombination sequence(s) and a selection marker gene are co-located on the same vector or DNA segment, which is introduced into the target locus, e.g., by any method mentioned above (homologous recombination, random integration, etc.). As the expression level of the selection marker gene correlates with the transcription activity at the integration site, cells showing a high expression level at site of integration, cell robustness, and good growth characteristics, e.g., in a bioreactor, can be identified very effectively. The level of expression of the selection marker gene can be determined by methods well known in the art, e.g., on the basis of either the amount of corresponding mRNA that is present in the cell, or the amount of polypeptide encoded by the gene. For example, mRNA transcribed from the introduced gene sequence can be quantified by Northern blot hybridization, ribonuclease RNA protection, in situ hybridization to cellular RNA or by PCR (see Sambrook et al., 1989; Ausubel et al., 1994, supra). Proteins encoded by a selected sequence can be quantified by various methods, e.g., by ELISA, by Western blotting, by radioimmunoassays, by immunoprecipitation, by assaying for the biological activity of the protein, by immunostaining of the protein followed by FACS analysis, or by measuring the fluorescence signals of a fluorescent protein (see Sambrook et al., 1989; Ausubel et al., 1994 updated, supra). By such a method excellent candidates of a production cell line for producing biopharmaceuticals may be obtained.

The integrated recombination sequence(s) (first recombination sequence(s)) allow integration of a further DNA molecule, e.g., a vector or DNA segment carrying at least one further recombination sequence (second recombination sequence) via sequence-specific recombination by a bacteriophage lambda integrase Int into a transcriptional active locus. Preferably, that further DNA molecule comprising at least one second recombination sequence further comprises an expression cassette for the expression of at least one biopharmaceutically relevant gene of interest. For this, host cells, which comprise the first integrated recombination sequence, preferably integrated into the host cell genome at a transcriptional active locus, are tranfected with a DNA molecule comprising the second recombination sequence for a bacteriophage lambda integrase Int, and are cultivated under conditions that allow sequence-specific recombination between the first and the second recombination sequence, preferably the integration of the DNA molecule comprising the second recombination sequence into the host cell genome comprising the first recombination sequence. First and second recombination sequences can be either attP, attB, attL, attR or any derivative thereof, which allows sequence-specific recombination by a bacteriophage lambda integrase Int or any functional mutant thereof. For example, if the first recombination sequence comprises attP or a derivative thereof second may comprises attB, attL, attR or any derivative thereof.

Preferred is the method wherein the sequence-specific recombination is performed by Int, or by Int and XIS, FIS and/or IHF. Most preferred is the method wherein the sequence-specific recombination is performed by Int or by Int and a XIS factor, or by Int and IHF, or by Int and XIS and IHF. Further preferred is the method wherein the sequence-specific recombination is performed by a modified Int, preferably the Int-h or Int-h/218. In this context, use of a modified Int together with XIS and/or IHF is also within the meaning of the present invention.

By this approach any DNA sequence(s), comprising a second recombination sequence for the bacteriophage lambda integrase Int is/are integrated into a known, well characterized and defined locus of the host cell. To select for cells where a sequence-specific recombination has occurred one can introduce, for example, a non-functional expression cassette comprising the selection marker gene, e.g., without a promoter or promoter/enhancer or only part of the coding region of the gene. Only if sequence-specific recombination has occurred, a complete and functional expression cassette with efficient expression of the selection marker gene will be generated, thus allowing for the selection of cells having integrated the gene of interest via sequence specific integration.

By the method of the present invention production cell lines are obtainable differ from the host cell merely by the identity of DNA sequences integrated at a defined site of integration, e.g., into a genomic locus. Due to less genetic variation between different cell clones a more generic process for the development of production cell lines can be used, thus reducing time and capacity for clone selection and development of an optimized production process. The production cell lines may be used for the manufacturing of the desired polypeptide(s).

A further aspect of the present invention therefore relates to a method of producing at least one gene product of interest in a eukaroytic cell, comprising:
 a) introducing a first DNA comprising an attB, attP, attL or attR sequence or a derivative thereof into a cell;
 b) introducing a second DNA comprising an attB, attP, attL or attR sequence or a derivative thereof, and at least one gene of interest into a cell,
 c) contacting said cell with a bacteriophage lambda integrase Int;
 d) performing the sequence-specific recombination by a bacteriophage lambda integrase Int, wherein the second DNA is integrated into the first DNA; and
 e) cultivating said cell under conditions, wherein the gene product(s) of interest is/are being produced.

Preferred is that method, wherein if said first DNA sequence comprises an attB sequence or a derivative thereof said second sequence comprises an attB, attL or attR sequence or a derivative thereof, or wherein if said first DNA sequence comprises an attP sequence or a derivative thereof said second sequence comprises an attP, attL or attR sequence or a derivative thereof, or wherein if said first DNA sequence comprises an attL sequence or a derivative thereof said second sequence comprises an attB, attP or attL sequence or a derivative thereof, or wherein if said first DNA sequence comprises an attR sequence or a derivative thereof said second sequence comprises an attB, attP or attR sequence or a derivative thereof.

In a more preferred embodiment of that method, the first DNA has been integrated into the genome, an artificial-/ minichromosome or an episomal element of a host cell, preferably at sites showing high transcription activity, before said second DNA is introduced into said cell.

The present invention also relates to a method of producing at least one or more gene products of interest in a host cell, wherein said host cell comprises one attB, attP, attL or attR sequence or a derivative thereof integrated into the genome of said host cell comprising:
 a) introducing a DNA comprising an attB, attP, attL or attR sequence or a derivative thereof, and at least one gene of interest into said cell,
 b) contacting said cell with a bacteriophage lambda integrase Int;
 c) performing the sequence-specific recombination by a bacteriophage lambda integrase Int, wherein the second DNA is integrated into the first DNA;
 d) cultivating said cell under conditions, wherein the gene product(s) of interest is/are being produced.

The method may be carry out not only with an attB, attP, attL or attR sequence or a derivative thereof being integrated into a host cell genome by genetic engineering of said cell, but also with naturally occurring recombination sequence of the genome, e.g., the attH-site described in WO 01/16345 (5'-GAAATTCTTTTTGATACTAACTTGTGT-3'; SEQ ID NO:17) or any other recombination sequence, which allows sequence-specific recombination mediated by an Int or any functional mutant thereof.

Those methods are preferred, wherein said sequence-specific recombination is performed by Int or by Int and a XIS factor, or by Int and IHF, or by Int and XIS and IHF. Further preferred is the method wherein the sequence-specific recombination is performed by a modified Int, preferably the Int-h or Int-h/218. In this context, use of a modified Int together with XIS and/or IHF is also within the meaning of the present invention. Int, Int-h or Int-h/218, XIS, and/or IHF may be added to the cell in purified form or being co-expressed by said host cell, wherein the sequence-specific recombination is being performed.

A further embodiment of the above mentioned methods relates to a method, wherein the polypeptide(s)/product(s) which is/are encoded by the gene(s) of interest and being produced in said host cell, is/are isolated from the cells or the cell culture supernatant, if secreted into the culture medium.

Production cells are cultivated preferentially in serum-free medium and in suspension culture under conditions which are favorable for the production of the desired gene(s) and isolating the protein of interest from the cells and/or the cell culture supernatant. Preferably the protein of interest is recovered from the culture medium as a secreted polypeptide, or it can be recovered from host cell lysates if expressed without a secretory signal. It is necessary to purifiy the protein of interest from other recombinant proteins, host cell proteins and contaminants in a way that substantially homogenous preparations of the protein of interest are obtained. As a first step often cells and/or particulate cell debris are removed from the culture medium or lysate. The product of interest thereafter is purified from contaminant soluble proteins, polypeptides and nucleic acids, for example, by fractionation on immunoaffinity or ion-exchange columns, ethanol precipitation, reverse phase HPLC, Sephadex chromatography on silica or on a cation exchange resin such as DEAE. In general, methods teaching a skilled persion how to purify a heterologous protein expressed by host cells, are well known in the art. Such methods are for example described by Harris et al. (1995) and Scopes (1988). Therefore, the aforementioned method of expressing at least one gene of interest may be added by an additional purification step, wherein the desired polypeptide is purified from the host cells or from cell culture if secreted into the culture medium.

The method of the present invention may be performed in all eukaryotic cells. Cells and cell lines may be present, e.g., in a cell culture and include but are not limited to eukaryotic cells, such as yeast, plant, insect or mammalian cells. For example, the cells may be oocytes, embryonic stem cells, hematopoietic stem cells or any type of differentiated cells. A method is preferred wherein the eukaryotic cell is a mammalian cell. More preferred is a method wherein the mammalian cell is a human, simian, murine, rat, rabbit, hamster, goat, bovine, sheep or pig cell. Preferred cell lines or "host cells" for the production of biopharmaceuticals are human, mice, rat, monkey, or rodent cell lines. More preferred are hamster cells, preferably BHK21, BHK TK-, CHO, CHO-K1, CHO-DUKX, CHO-DUKX B1, and CHO-DG44 cells or the derivatives/progenies of any of such cell lines. Particularly preferred are CHO-DG44, CHO-DUKX, CHO-K1 and BHK21, and even more preferred CHO-DG44 and CHO-DUKX cells. Furthermore, murine myeloma cells, preferably NS0 and Sp2/0 cells or the derivatives/progenies of any of such cell lines are also known as production cell lines.

Host cells are most preferred, when being established, adapted, and completely cultivated under serum free conditions, and optionally in media which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-SFMII (Invtirogen), serum-free CHO Medium (Sigma), and protein-free CHO Medium (Sigma) are exemplary appropriate nutrient solutions. Any of the media may be supplemented as necessary with a variety of compounds examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing a selectable gene a suitable selection agent is added to the culture medium.

"Desired proteins/polypeptides" or "proteins/polypeptides of interest" of the invention are for example, but not limited to insulin, insulin-like growth factor, hGH, tPA, cytokines, such as interleukines (IL), e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL; G-CSF, GM-CSF, M-CSF, MCP-1 and VEGF. Also included is the production of erythropoietin or any other hormone growth factors and any other polypeptides that can serve as agonists or antagonists and/or have therapeutic or diagnostic use. The method according to the invention can also be advantageously used for production of antibodies, such as monoclonal, polyclonal, multispecific and single chain antibodies, or fragments thereof, e.g., Fab, Fab', F(ab')2, Fc and Fc'-fragments, heavy and light immunoglobulin chains and their constant, variable or hypervariable region as well as Fv- and Fd-fragments (Chamov et al., 1999).

Fab fragments (Fragment antigen-binding=Fab) consist of the variable regions of both chains which are held together by the adjacent constant region. These may be formed by protease digestion, e.g., with papain, from conventional antibodies, but similar Fab fragments may also be produced in the mean time by genetic engineering. Further antibody fragments include F(ab')2 fragments, which may be prepared by proteolytic cleaving with pepsin.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilised. It is advantageous to link the variable regions of the heavy and of the light chain by a short peptide fragment, e.g., of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins of this kind known from the prior art are described in Huston et al. (1988).

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g., the CH3 region of an IgG or coiled coil structure (helix structures) such as Leucin-zipper domains. However, there are also strategies in which the interaction between the VH/VL regions of the scFv are used for the multimerisation (e.g., dia-, tri- and pentabodies). By diabody the skilled person means a bivalent homodimeric scFv derivative. The shortening of the Linker in an scFv molecule to 5-10 amino acids leads to the formation of homodimers in which an inter-chain VH/VL-superimposition takes place. Diabodies may additionally be stabilised by the incorporation of disulphide bridges. Examples of diabody-antibody proteins from the prior art can be found in Perisic et al. (1994).

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g., also from IgG1) and a Linker region. Examples of minibody-antibody proteins from the prior art can be found in Hu et al. (1996).

By triabody the skilled person means a: trivalent homotrimeric scFv derivative (Kortt et al. (1997)). ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures (Pack et al., 1993; Lovejoy et al., 1993; Pack et al., 1995). In a preferred embodiment of the present invention, the gene of interest is encoded for any of those desired polypeptides mentioned above, preferably for a monoclonal antibody, a derivative or fragment thereof.

In order to perform any embodiment of the present invention, an integrase has to act on the recombination sequences.

The integrase or the integrase gene and/or a co-factor or a co-factor gene, e.g., the XIS factor or the XIS factor gene and/or IHF or the IHF gene may be present in the eukaryotic cell already before introducing the first and second recombination sequence. They may also be introduced between the introduction of the first and second recombination sequence or after the introduction of the first and second recombination sequence. Purification of recombinase and host factor proteins has been described in the art (Nash, 1983; Filutowicz et al., 1994). In cases when they are not known, cell extracts can be used or the enzymes can be partially purified using procedures described for example for Int or Cre recombinase. The purified proteins can be introduced into a cell by standard techniques, for example by means of injection or microinjection or by means of a lipofection as described in Example 2 of the present invention for IHF. The integrase used for the sequence-specific recombination is preferably expressed in the cell in which the reaction is carried out. For that purpose a third DNA sequence comprising an integrase gene is introduced into the cells. If the sequence specific recombination is carried out, e.g., with attL/attR a XIS factor gene (fourth DNA sequence) may be introduced into the cells in addition. Most preferred is a method wherein the third and/or fourth DNA sequence is integrated into the eukaryotic genome of the cell or an artificial-/minichromosome via homologous recombination or randomly. Further preferred is a method wherein the third and/or fourth DNA sequence comprises regulatory sequences resulting in a spatial and/or temporal expression of the integrase gene and/or XIS factor gene.

In this case a spatial expression means that the Int recombinase, the XIS factor, and/or the IHF factor, respectively, is expressed only in a particular cell type by use of cell type specific promotors and catalyzes the recombination only in these cells, e.g., in liver cells, kidney cells, nerve cells or cells of the immune system. In the regulation of the integrase/XIS factor/IHF expression a temporal expression may be achieved by means of promotors being active from or in a particular developmental stage or at a particular point of time in an adult organism. Furthermore, the temporal expression may be achieved by use of inducible promoters, e.g., by interferon or tetracycline depended promotors; see review of Müller (1999).

The integrase used in the method of the present invention may be both the wild-type and the modified (mutated) integrase of the bacteriophage lambda. As the wild-type integrase is only able to perform the recombination reaction at a high efficiency with a co-factor, namely IHF, it is preferred to use a modified integrase in the method of the present invention. If the wild-type integrase is used in the method of the present invention, IHF may be needed in addition to achieve a stimulation of the recombination reaction. The modified integrase is modified such that said integrase may carry out the recombination reaction without IHF or other host factors such as XIS and FIS. For example, a recombination reaction between attL and attR sequences may be preformed by a modified Int without the addition of a host factor (see results 5.1 and FIGS. 2C and 2D).

The generation of modified polypeptides and screening for the desired activity is state of the art and may be performed easily; Erlich (1989). Stockton Press. For example, a nucleic acid sequence encoding for a modified integrase is intended to include any nucleic acid sequence that will be transcribed and translated into an integrase either in vitro or upon introduction of the encoding sequence into bacteria or eukaryotic cells. The modified integrase protein encoding sequences can be naturally occurring (by spontaneous mutation) or recombinantly engineered mutants and variants, truncated versions and fragments, functional equivalents, derivatives, homologs and fusions of the naturally occurring or wild-type proteins as long as the biological functional activity, meaning the recombinase activity, of the encoded polypeptide is maintained. Recombinase activity is maintained, when the modified recombinase has at least 50%, preferably at least 70%, more preferred at least 90%, most preferred at least 100% of the activity of the wild-type integrase Int, measured in a co-transfection assay with substrate vectors and expression vectors as described in results 5.1 of the present invention or in Example 3 of WO 01/16345. Certain amino acid sequence substitutions can be made in an integrase or its underlying nucleic acid coding sequence and a protein can be obtained with like properties. Amino acid substitutions that provide functionally equivalent integrase polypeptides by use of the hydropathic index of amino acids (Kyte et al., 1982) can be prepared by performing site-specific mutagenesis or polymerase chain reaction mediated mutagenesis on its underlying nucleic acid sequence. In the present invention mutants or modified integrases are preferred, which show in comparison to a wild-type protein improved recombinase activity/recombination efficiency or an recombination activity independent of one or more host factors. "Wild-type protein" means a complete, non truncated, non modified, naturally occurring gene of the encoding polypeptide. Two Int mutants preferred are bacteriophage lambda integrases designated as Int-h and Int-h/218; Miller et al. (1980); Christ and Dröge, (1999). Int-h includes a lysine residue instead of a glutamate residue at position 174 in comparison to wild-type Int. Int-h/218 includes a further lysine residue instead of a glutamate residue at position 218 and was generated by PCR mutagenesis of the Int-h gene. Said mutants may catalyze the recombination between attB/attB, attP/attP, attL/attL or attR/attR and all other possible combinations, e.g., attP/attR, attL/attP, attL/attB, or attR/attB or the derivatives thereof without the co-factors IHF, XIS, and/or FIS and negative supercoiling in $E.\ coli$, in eukaryotic cells, and in vitro, i.e., with purified substrates in a reaction tube. An improvement of the efficiency of the recombination may be achieved with a co-factor, e.g., FIS. The mutant Int-h/218 is preferred, because this mutant catalyze the recombination reaction with increased efficiency.

If the first reaction leads to an excision and the used two recombination sequences are identical, e.g., attP/P, the resulting recombination sequences after the recombination will be identical to those on the substrate, e.g., here two attP sequences. If however, the two partner sequences are different, e.g., attP/R, the recombination reaction will generate hybrid recombination sequences which comprise one functional half from one sequence (e.g. attP) and one half from the other (attR). A functional half recombination site can be defined as the sequence either 5' or 3' form the overlap, whereby the overlap is considered, in each case, as a part of a funtional half-site. If the respective overlap region of the used recombination sequences is identical the excision reaction may be performed with any recombination sequence according to the invention. Additionally, the overlap region designates the orientation of the recombination sequences to each other also, i.e., inverted or direct. The reaction may be performed with wilt-type Int with low efficiency only, however, the addition of IHF or in the absence of IHF the presence of arm binding site(s) in addition to the core binding site stimulates and increases the efficiency. The reaction may be performed without any cofactor by a modified Int.

Furthermore, a method is preferred wherein a further DNA sequence comprising a Xis factor gene is introduced into the cells. Most preferred is a method wherein the further DNA sequence further comprises a regulatory DNA sequence giving rise to a spatial and/or temporal expression of the Xis factor gene.

For example, after successful integrative intramolecular recombination (inversion) by means of Int leading to the activation/inactivation of a gene in a particular cell type said gene may be inactivated or activated at a later point of time again by means of the induced spatial and/or temporal expression of XIS with the simultaneously expression of Int.

Furthermore, the invention relates to the use of any recombination sequences or the derivative thereof, e.g., to the derivative of attP as specified in SEQ ID NO:2 in a sequence specific recombination of DNA in eukaryotic cells. The eukaryotic cell may be present in a cell aggregate of an organism, e.g., a mammal, having no integrase or Xis factor in its cells. Said organism may be used for breeding with other organisms having in their cells the integrase or the Xis factor so that off-springs are generated wherein the sequence specific recombination is performed in cells of said off-springs. Thus, the invention relates also to the use of an integrase or an integrase gene and a Xis factor or a Xis factor gene and an IHF factor or an IHF factor gene in a sequence specific recombination in eukaryotic cells. Furthermore, the present invention relates to eukaryotic cells and cell lines in which the method of the present invention was performed, wherein said cells or cell lines are obtained after performing the method of the present invention.

The practice of the present invention will employ, unless otherwise indicated, conventional techniques of cell biology, molecular biology, cell culture, immunology and the like which are in the skill of one in the art. These techniques are fully disclosed in the current literature. (See e.g., Sambrook et al., 1989; Ausubel et al., 1994, updated; Brown, 1991; Goeddel, 1991; Bothwell et al., 1990; Wu et al., 1989; Kriegler, 1990; McPherson et al., 1991; Gait, 1984; Miller and Calos, 1987; Butler, (1991); Pollard et al., 1990; Freshney et al., 1987; Studzinski, 1995; Melamed et al., eds., Flow Cytometry and Sorting, Wiley-Liss (1990); Current Protocols in Cytometry, John Wiley & Sons, Inc. (updated); Wirth and Hauser, Genetic Engineering of Animals Cells, in: Biotechnology Vol. 2, Pühler ed., VCH, Weinheim 663-744; the series Methods of Enzymology (Academic Press, Inc.), and Harlow et al., eds., Antibodies: A Laboratory Manual (1988).

All publications and patent applications mentioned in this specification are indicative of the level of skill of those skilled in the art to which this invention pertains. All publications and patent applications cited herein are hereby incorporated by reference in their entirety in order to more fully describe the state of the art to which this invention pertains. The invention generally described above will be more readily understood by reference to the following examples, which are hereby included merely for the purpose of illustration of certain embodiments of the present invention and are not intended to limit the invention in any way.

EXAMPLES

1. Production of Expression and Substrate Vectors

The construction of mock and Int expression vectors pCMV, pCMVSSInt, pCMVSSInt-h, and pCMVSSInt-h/218 have been described; Lorbach et al. (2000). Int expression is driven by the human cytomegalovirus promoter.

Substrate vectors used in intramolecular recombination assays, containing attB/attP (pλIR) or attL/attR (PλER) as direct repeats, are derivatives of pGEM®4Z (Promega). pλIR was constructed by inserting attB as double-stranded oligonucleotide into ClaI/EcoRI-cleaved pPGKneo. This vectors is a derivative of pPGKSSInt-h, in which the Int-h gene was replaced by a neomycin gene (neo) using PstI/XbaI. The CMV promoter plus a hybrid intron was generated by PCR using pCMVSSInt as template and cloned into the KpnI/ClaI-cleaved, attB-containing pPGKneo vector. This CMV-attB-neo-expression cassette was then cloned by PCR into BamHI-cleaved pGEM®4Z. The attP site, containing an A-to-C substitution in the P'-arm which deletes a translational stop signal, was generated by assembly PCR using primers:

```
(attP01)
5'-GTCACTATCAGTCAAAATACAATCA-3',      (SEQ ID NO: 3)

(attP02)
5'-TGATTGTATTTTGACTGATAGTGAC-3',      (SEQ ID NO: 4)

(PFP-NsiI)
5'-
CCAATGCATCCTCTGTTACAGGTCACTAATAC-3', (SEQ ID NO: 5)
and (P'RP-EcoRV-NotI)
5'-ATAAGAATGCGGCCGCAGATATCAGG         (SEQ ID NO: 6)
GAGTGGGACAAAATTGAA-3'.
``` pGFPattB/attP was used as template (Lorbach et al. (2000), supra). The PCR fragment was cleaved with NsiI and NotI and ligated to the 3'-end of a BamHI/PstI-fragment containing a transcriptional stop cassette, which was generated from pBS302 (Gibco/BRL). The GFP gene and the polyA signal was cloned by PCR using pCMVSSGFP (a derivative of pCMVSSInt-h, in which the Int-h gene is replaced by eGFP using PstI/XbaI). The GFP-containing PCR fragment was cleaved with NotI and XbaI and was then ligated together with the BamHI/NotI-cleaved transcriptional stop/attP fragment into the BamHI/XbaI-cleaved vector already containing the CMV promoter, attB, and the neo expression cassette. pλER was constructed as pλIR, except that attL was generated by PCR using pGFPattL/attR (Lorbach et al. (2000), supra) as template, and was cloned into the ClaI/EcoRI-cleaved pPGKneo. The attR site was generated by PCR using pGFPattL/attR as template, and the product was cleaved with NsiI and NotI.

Substrate vectors for intermolecular recombination assays which contain the CMV promoter in front of different attachment sites: pCMVattPmut contains three G-to-C substitutions in the P-arm. These changes were necessary to eliminate ATG start codons that would prevent GFP expression after recombination. The substitutions are outside of protein binding sites in attP and were introduced by assembly PCR. First, two overlapping PCR products were generated, one with primer pair attP-ATC-1/attP-2 and one with attP-ATC-3/attP-4. pGFPattB/attP was used as template. PCR products were gel-purified and used as templates for PCR with primers attP-PstI and attP-XbaI. The resulting product was digested with PstI and XbaI, and cloned into pCMVSSInt. The primer sequences for assembly PCR are:

```
                                      (SEQ ID NO: 7)
(attP-    5'-tttggataaaaaacagactagataatactgtaaaaca
ATC-1)    caagatatgcagtcacta-3', (SEQ ID NO: 8)
(attP-2)  5'-taacgcttacaatttacgcgt-3', (SEQ ID NO: 9)
(attP-    5'-ctgcatatcttgtgttttacagtattatctagtctg
ATC-3)    tttttatccaaaatctaa-3',
```

```
                                          (SEQ ID NO: 10)
(attP-4)    5' ctggacgtagccttcgggcatggc-3', (SEQ ID NO: 11)
(attP-      5'-gactgctgcagctctgttacaggtcac-3',
PstI)

(SEQ ID NO: 12)
(attP-      5'-gactgtctagagaaatcaaataatgat-3'.
XbaI)
``` pCMVattB was generated by inserting attB as double-stranded oligonucleotide into Pst/XbaI-cleaved pCMVattP-mut. pCMVattL was generated by PCR using pλER as template for attL, which was introduced into PstI/XbaI-cleaved pCMVattPmut.

Vectors which contain a transcriptional stop signal and an att site placed in front of a promoterless GFP gene were constructed as follows: pWSattBGFP was generated by first deleting a part of the hygromycin gene from pTKHyg (Clontech) using AvaI and NdeI. The vector backbone was ligated after the sticky ends were made blunt by Klenow polymerase. An attB-GFP fragment, generated by PCR, was cloned into MfeI and HindIII sites, thereby creating a new NheI site 5' of attB. Finally, the transcriptional stop sequence was inserted through restriction with EcoRI and NheI. pWSattRGFP was generated by isolating the BamHI/NotI transcriptional stop-attR fragment from pXER, which was inserted into pWSatt-BGFP cleaved with the same enzymes. pWSattPGFP was generated by PCR of the attP site using pGFPattP/attB as template, which was inserted into pWSattBGFP cleaved with EcoRI/NotI thus replacing attB. Plasmids were isolated from *E. coli* strain XL1-Blue using affinity chromatography (Qiagen). The nucleotide composition of relevant genetic elements was verified by DNA sequencing using the fluorescence-based 373A system (Applied Biosystems).

2. Cell Culture, Recombination Assays, and Flow Cytomery

HeLa cells were cultured in Dulbecco's modified eagle medium (DMEM) supplemented with 10% fetal calf serum, streptomycin [0.1 mg/ml] and penicillin [100 U/ml]. Cells were passaged twice before transfection.

Typical recombination assays were performed as follows. Cells were harvested, washed with PBS and resuspended in RPMI 1640 without L-glutamine and phenol red (Life Technologies). A total of 60 µg of expression and substrate vectors at a molar ratio of 1:1 were then introduced into approximately $1 \times 10^7$ cells at 300V and 960 µF using a Gene pulser (Bio-Rad). After electroporation, cells were plated in an appropriate dilution on 10 cm dishes. A single-cell suspension was prepared at 24, 48, and 72 hrs after transfection. Dead cells were excluded from the analysis by staining with 7-amino-actinomycin D (Sigma), and cells were analyzed by FACScalibur (Becton Dickinson). FACS data were analyzed with CellQuest™ software. The transfection efficiencies for intermolecular recombination assays were determined for each experiment were co-transfecting 40 µg pCMV with 20 µg pEGFP-C1 (Clontech); those for intramolecular recombination were determined with 30 µg pCMV and 30 µg pEGFP-C1.

Experiments involving purified IHF were performed by introducing first 30 µg of Int expression vectors to approximately 6×106 cells via electroporation as described above. After 3 to 4 hrs, about 1×105 cells were transfected with 2 µg of substrate vectors for intramolecular recombination, or with a total of 2 µg of substrate vectors at a molar ratio of 1:1 for intermolecular recombination. Substrates were pre-incubated at room temperature with 2 µg purified IHF (Lange-Gustafson and Nash, J Biol Chem. Oct. 25, 1984; 259(20): 12724-32) in a low salt buffer (50 mM NaCl, 10 mM Tris-HCl, pH 8.0, 1 mM EDTA) for at least 30 minutes. Transfection of IHF-DNA complexes was achieved with FuGene (Boehringer Mannheim) and the efficiencies were always in the range of 80%. Cells were analyzed by flow cytometry after additional 48 hrs as described above.

3. Results

3.1 Kinetics of Intra- and Intermolecular Recombination Reactions

As showed in the inventors' previous studies, mutant Int catalyzed intramolecular integrative and excisive recombination reactions in the absence of natural accessory factors in *E. coli* and in human cells (Christ et al., 1999, supra; Lorbach et al., 2000, supra). However, an interesting question with respect to interactions of episomal DNA segments inside mammalian cells concerns the ability of mutant Int to perform intermolecular recombination, i.e., when two recombination sites are located on different DNA molecules in trans. The inventors compared therefore first intra- and intermolecular integrative recombination reactions.

Figure 2:
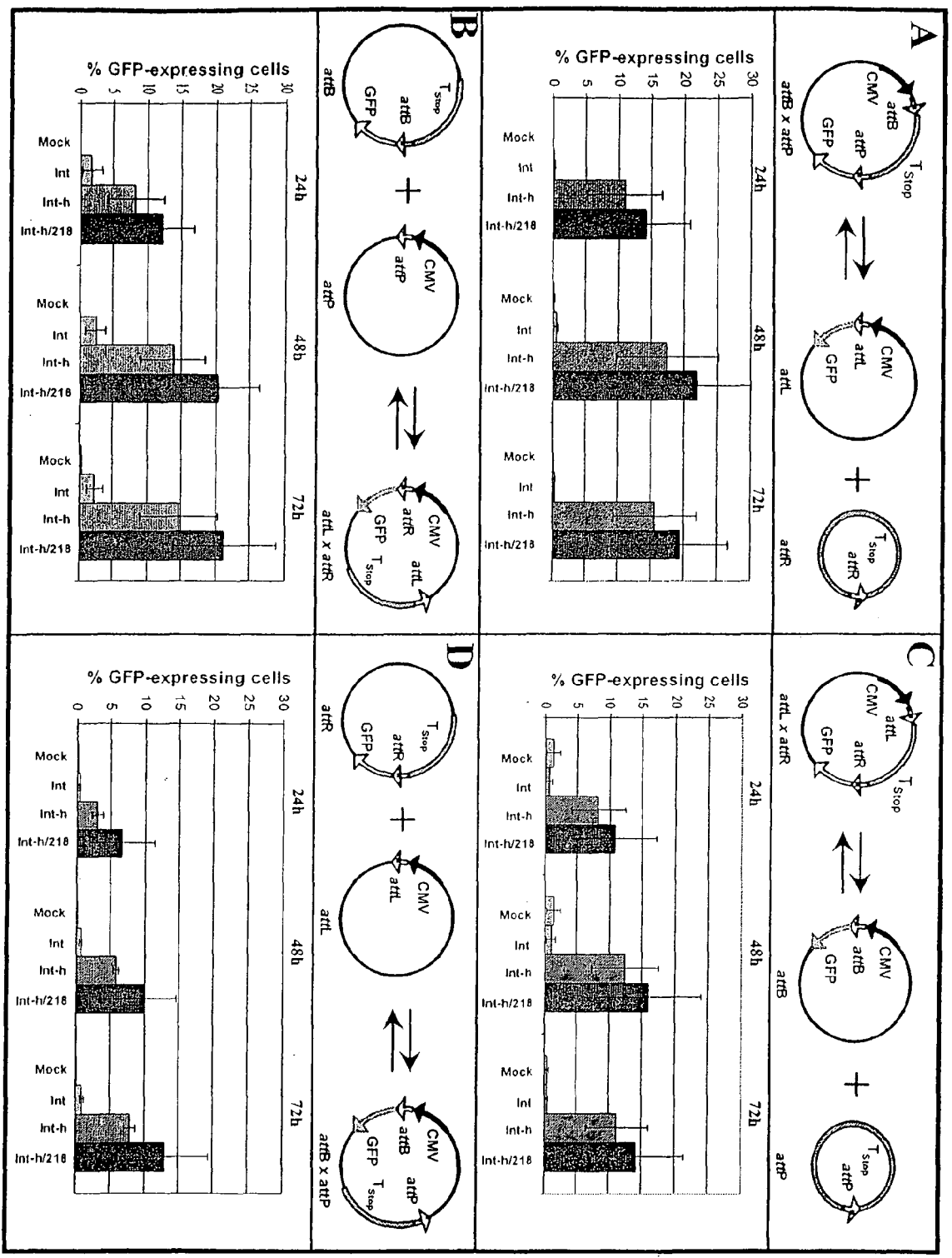
FIGS. 2A-D show intra- and intermolecular recombination reactions.

Intramolecular recombination was tested with a substrate that contains attB and attP as direct repeats flanking a transcriptional stop signal. This recombination cassette, in turn, is flanked by a CMV promoter and the coding region for GFP. Recombination between attB and attP generates hybrid sites attL and attR, and leads to excision of the stop signal. Subsequent expression of the GFP gene thus serves as reporter of recombination (FIG. 2A, top).

Expression vectors for either Int, Int-h, or Int-h/218 were co-transfected with the substrate vector into HeLa cells. The expression vector backbone (mock) was used as negative control. Transfection efficiencies independently determined for each experiment were in the range of 95 to 98% (data not shown). FACS analyses from 3 studies show that both mutant Int efficiently catalyzed recombination, leading in some experiments to about 30% GFP-expressing cells (FIG. 2A, bottom). The nucleotide sequence of recombination products, determined indirectly by DNA sequencing of PCR fragments, confirmed that the strand-transfer-reactions catalyzed by mutant Int generated the expected hybrid att sites (data not shown).

It is apparent that the double mutant Int-h/218 was more active than Int-h, whereas wild-type Int was almost inactive. The fraction of GFP-expressing cells increased during 48 hrs after transfection and remained steady for the next 24 hrs. The time course of the reactions also indicates that a majority of recombination events must have occurred within the first 24 hrs. This correlates well with the time course of Int-h/218 expression in HeLa cells (data not shown). Although the inventors cannot exclude the possibility that a fraction of GFP-expressing cells resulted from inter- instead of intramolecular integrative recombination, the data set can be used as a reference for our analysis of intermolecular recombination.

The inventors analyzed intermolecular integrative recombination by placing attB and attP on separate plasmids. Recombination translocates the CMV promoter to a position upstream of the GFP gene (FIG. 2B, top). Hence, only intermolecular recombination between attB and attP will generate GFP-expressing cells. FACS analyses after co-transfection of the two substrate vectors with Int expression vectors yielded results which are comparable to those generated with substrates for intramolecular recombination (FIG. 2B, bottom). Again, the majority of recombination events must have occurred within the first 24 hrs after transfection and Int-h/218 was more active than Int-h. Wild-type Int generated only a very small fraction of GFP-expressing cells. These results demonstrate that over a time course of 24 to 72 hrs, intermolecular integrative recombination by mutant Int is at least as efficient as the corresponding intramolecular reaction.

The same experimental strategy was then employed to compare intra- and intermolecular excisive (attLxattR) recombination pathways. The results revealed again that intermolecular recombination by mutant Int was as efficient as intramolecular recombination (FIGS. 2C and D). The efficiency of excisive recombination reactions, however, was slightly reduced compared to integrative recombination. Recombination by wild-type Int was again barely detectable.

3.2 DNA Arm-Binding Sites in att are not Required, but Stimulate Recombination

The results so far show that mutant Int catalyzed integrative and excisive recombination on episomal substrates in a significant number of transfected cells. In contrast, recombination activities of wild-type Int was barely detectable above background. Since excisive recombination by wild-type Int depends on the presence of protein co-factors IHF and XIS, but does not require negative DNA supercoiling, this result demonstrates that eukaryotic counterparts of these co-factors are lacking in human cells. Further, it is known that episomal substrates are topologically relaxed soon after transfection (Schwikardi et al., 2000). It appears, therefore, that mutant Int perform recombination without the formation of defined nucleoprotein complexes, such as the intasome assembled at attP. This raises the question of the functional role of DNA arm-binding sites in recombination. They were present in at least one of the partner att sites employed so far.

Figure 3:
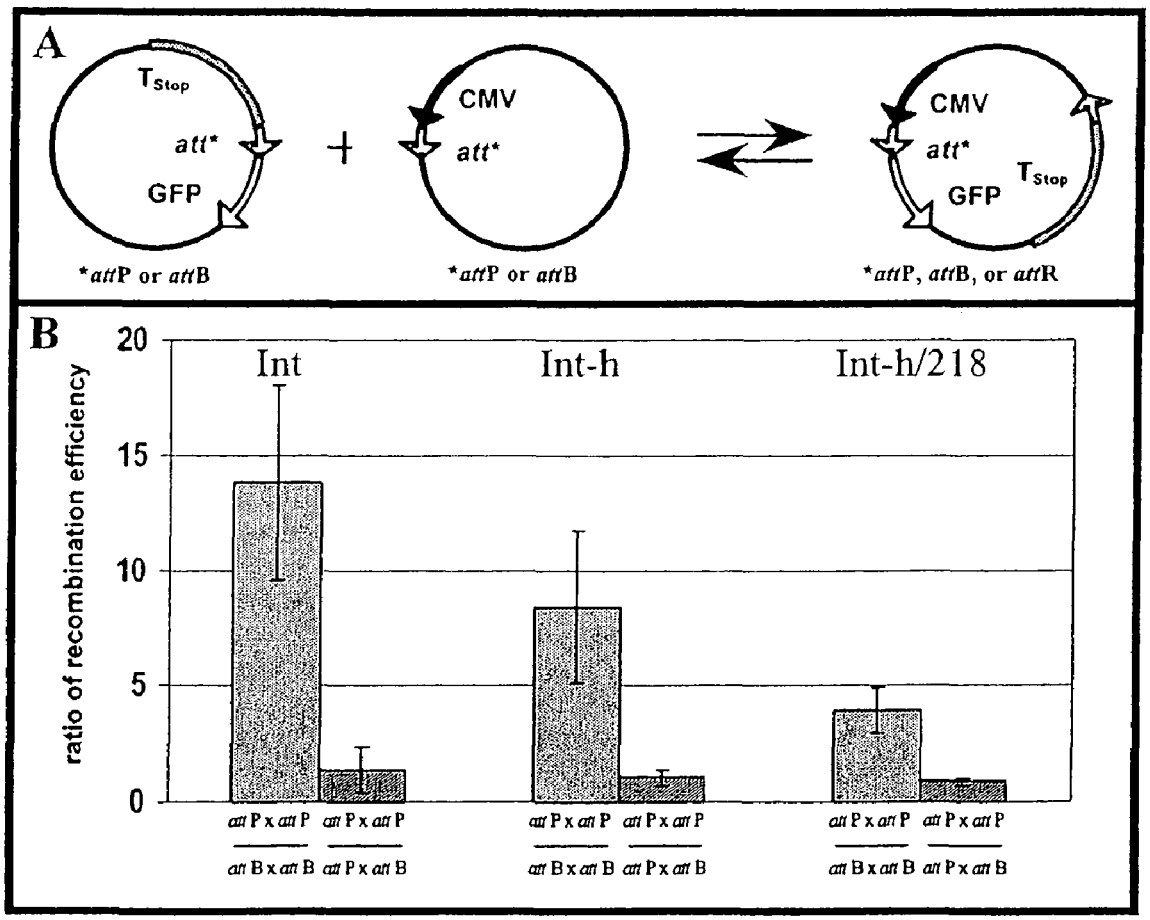
FIGS. 3A-B show that the presence of Int arm-binding DNA sequences in att sites stimulates intermolecular recombination.

In order to investigate this question, we used intermolecular recombination with pairs of substrate vectors containing attB or attP in various combinations (FIG. 3A). The fraction of GFP-expressing cells that results from recombination was determined by FACS at 48 hrs after co-transfection with Int expression vectors. Transfection efficiencies were always above 90% (data not shown). The results from 3 experiments show that intermolecular recombination between pairs of attP was as efficient as recombination between attB and attP (FIG. 3B). However, only Int-h/218 utilized pairs of attB sites as substrate to a significant extent. The efficiency of this reaction was, on average, about four-fold reduced compared to reactions between attP and attP or attB and attP (FIG. 3B) Hence, the fraction of GFP-expressing cells that results from recombination between two attB sites dropped to a level of 4 to 5%. These results demonstrate that the presence of arm-type sequences in att sites is not required for recombination by Int-h/218, but significantly stimulates the reaction. This stimulatory effect is even more pronounced (about eight-fold) when Int-h was used. Further, the residual recombination activity observed with wild-type Int appears highly dependent on the presence of arm binding sites.

3.3 Recombination by Wild-Type Int is Stimulated by Transfected IHF Protein

Figure 4:
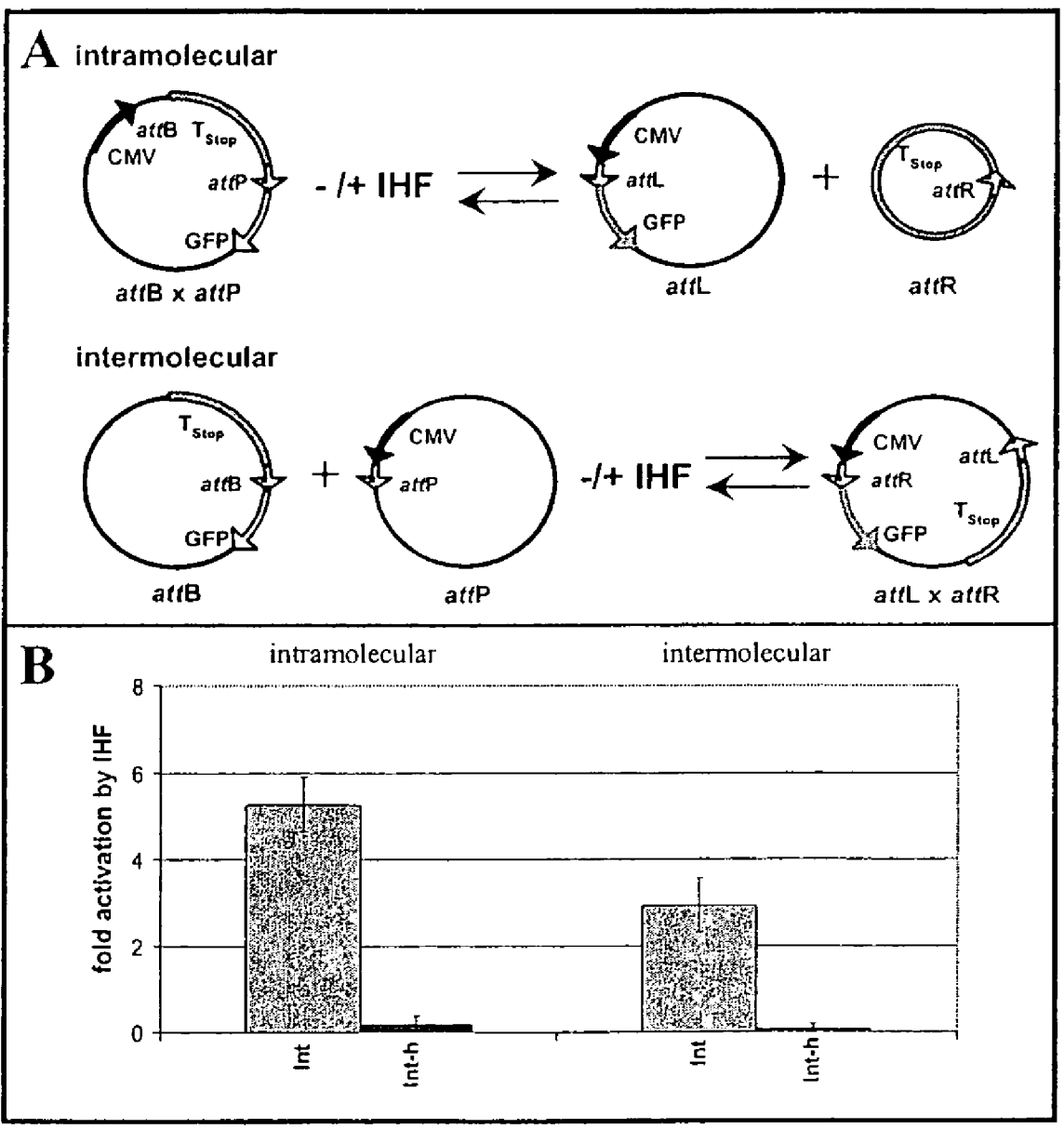
FIGS. 4A-B show that purified IHF protein stimulates intra- and intermolecular integrative recombination by wild-type Int.

Efficient integrative recombination catalyzed by wild-type Int in vitro and in *E. coli* requires the protein co-factor IHF and supercoiling of attP. The apparent lack of either co-factor in mammalian cells thus led us to investigate whether the residual recombination activity of wild-type Int is augmented if purified IHF, pre-incubated with a supercoiled substrate, is co-introduced into HeLa cells. To test this possibility, we introduced first expression vectors for either wild-type Int or Int-h. At 3 to 4 hrs after electroporation, substrates for intra- or intermolecular recombination were incubated either with or without purified IHF. Protein-DNA mixtures as well as protein-free control samples were then transfected using Fugene (FIG. 4A). The fractions of GFP-expressing cells were compared after additional 48 hrs.

The results from three experiments show that intramolecular recombination by wild-type Int was stimulated, on average, up to five-fold due to the presence of IHF. The fraction of GFP-positive cells increased, for example, in one experiment from about 1% in the absence of IHF to 6% in its presence. The stimulatory effect on intermolecular recombination was also significant, but less pronounced (about three-fold). At 48 hrs after transfection, the stimulation was specific for wild-type Int since the activity of Int-h was not affected. Importantly, controls showed that transfection efficiencies were also not affected by the presence of IHF protein (data not shown).

REFERENCES

The following references, to the extent that they provide exemplary procedural or other details supplementary to those set forth herein, are specifically incorporated herein by reference.

Altschul et al., *J. Molec. Biol.*, 215:403-410, 1990.
Ausubel et al. In: *Current Protocols in Molecular Biology*, Greene Publishing Associates and Wiley-Interscience, NY, 1994.
Bothwell et al., In: *Methods for Cloning and Analysis of Eukaryotic Genes*, Bartlett Publ., 1990.
Brown, In: *Essential Molecular Biology*, IRL Press, 1991.
Butler In: *Mammalian Cell Biotechnology*, 1991.
Capecchi, *Science*, 244:1288, 1989.
Chamov et al. In: *Antibody Fusion Proteins*, Wiley-Liss Inc, 1999.
Christ and Dröge, *J. Mol. Biol.*, 288:825, 1999.
Erlich, In: *PCR Technology*, Stockton Press, 1989.
Filutowicz et al., *Gene*, 147:149, 1994.
Freshney et al., In: *Culture of Animal Cells*, Alan R. Liss, 1987.
Gait, In: *Oligonucleotide Synthesis*, 1984.
Goeddel, In: *Gene Expression Technology*, Academic Press, 1991.
Gottesman and Weisberg, In: *The Bacteriophage Lambda*, Cold Spring Harbor Laboratory, 113, 1971.
Gu et al., *Science*, 265, pp. 103, 1994.
Hardy et al., *J. Virol.*, 71:1842, 1997.
Harlow and Lane, In: *Antibodies: A Laboratory manual*, Cold Spring Harbor Laboratory, 1988.
Harris et al., In: *Protein Purification: A Practical Approach*, Pickwood and Hames (Eds.), IRL Press, 1995.
Hoess et al., *J. Mol. Biol.*, 181:351, 1985.
Hu et al., *Cancer Res.*, 56:3055, 1996.
Huston et al., *Proc. Nat'l Acad. Sci. USA*, 16:5879, 1988.
Kikuchi and Nash, *J. Biol. Chem.*, 253:7149, 1978.
Kilby et al., *Trends Genet.*, 9:413, 1993.
Kortt et al., *Protein Engin.*, 10:423, 1997.
Kriegler, In: *Gene Transfer and Expression*, Stockton Press, 1990.
Kuhn et al., *Science*, 269:1427, 1995.
Kyte et al., *J. Mol. Biol.*, 157:105, 1982.
Landy and Ross, *Science*, 197:1147, 1977
Landy, *Annu. Rev. Biochem.*, 58:913, 1989.
Lorbach et al., *J. Mol. Biol.*, 296:1175, 2000.
Lovejoy et al., *Science*, 259:1288, 1993.

McPherson et al., In: *PCR: A Practical Approach*, IRL Press at Oxford University Press, 1991.

Melamed et al., In: *Flow Cytometry and Sorting*, Wiley-Liss, 1990.

Miller and Calos, In: *Gene Transfer Vectors for Mammalian Cells*, 1987.

Miller et al., *Cell*, 20:721, 1980.

Mizuuchi and Mizuuchi, *Proc. Natl. Acad. Sci. USA*, 77:3220, 1980.

Müller, *Mech. Develop.*, 82:3, 1999.

Nash, *Annu. Rev. Genet.*, 15:143, 1981.

Nash, *Methods of Enzymology*, 100:210, 1983.

Nussinov. and Weisberg, *J. Biomol. Struct. Dynamics*, 3:1134, 1986.

Pack et al., *J. Mol. Biol.*, 246:28, 1995.

Pack et al., *Biotechnology*, 11:1271, 1993.

Perisic et al. *Structure*, 2:1217, 1994.

Pollard et al., In: *Animal Cell Culture*, Humana Press, 1990.

Sambrook et al., In: *Molecular Cloning: A Laboratory Manual*, Cold Spring Harbor Laboratory, Cold Spring Harbor, N.Y., 1989.

Schwikardi et al., *FEBS Letters*, 471:147, 2000.

Scopes, In: *Protein Purification*, Springer Verlag, 1988.

Studzinski, In: *Cell Growth and Apoptosis, A Practical Approach*, IRL Press at Oxford University Presss, 1995.

Wirth and Hauser, In: *Genetic Engineering of Animals Cells*, Biotechnology Vol. 2, Pühler ed., VCH, Weinheim 663-744

WO 01/16345

WO 92/08796

WO 94/28143

Wu et al., In: *Recombinant DNA. Methodology*, Academic Press, 1989.

---

What is claimed is:

1. A method of promoting sequence specific recombination of a first DNA and a second DNA in a eukaryotic cell comprising:
  (a) providing the eukaryotic cell wherein the eukaryotic cell comprises the first DNA comprising an attB, an attP, an attL or an attR sequence;
  (b) introducing into the cell the second DNA comprising the attB, the attP, the attL or the attR sequence, wherein if said first DNA comprises the attB sequence, said second DNA comprises the attB, the attL or the attR sequence, or wherein if said first DNA comprises the attP sequence, said second DNA comprises the attP, the attL or the attR sequence, or wherein if said first DNA comprises the attL sequence, said second DNA comprises the attB, the attP or the attL sequence, or wherein if said first DNA comprises the attR sequence, said second DNA comprises the attB, the attP or the attR sequence; and
  (c) providing to the cell comprising the first DNA and the second DNA a bacteriophage lambda integrase Int under conditions that promote integrase-mediated sequence specific recombination between the first DNA and the second DNA.

2. The method according to claim 1, wherein the first recombination sequence is integrated into an artificial chromosome, a minichromosome or the genome of said cell.

3. The method according to claim 1, wherein said sequence-specific recombination is performed by the Int and one or more cofactors selected from XIS, FIS and/or IHF.

4. The method according to claim 3, wherein the Int, XIS, FIS and/or IHF are added to the cell in purified form or are co-expressed by said cell.

5. The method according to claim 1, wherein the Int is a modified Int.

6. The method according to claim 5, wherein the modified Int is Int-h or Int-h/218.

7. The method according to claim 5, wherein said sequence-specific recombination is performed by said modified Int and one or more cofactors selected from XIS, FIS and/or IHF.

8. A method of producing a polypeptide of interest in a eukaryotic cell comprising:
  (a) providing eukaryotic cell wherein the eukaryotic cell comprises a first DNA comprising an attB, an attP, an attL or an attR sequence;
  (b) introducing a second DNA comprising the attB, the attP, the attL or the attR sequence, and a segment encoding the polypeptide of interest into the cell, the segment operably linked to expression control sequences, wherein if said first DNA comprises the attB sequence, said second DNA comprises the attB, the attL or the attR sequence, or wherein if said first DNA comprises the attP sequence, said second DNA comprises the attP, the attL or the attR sequence, or wherein if said first DNA comprises the attL sequence, said second DNA comprises the attB, the attP or the attL sequence, or wherein if said first DNA comprises the attR sequence, said second DNA comprises the attB, the attP or the attR sequence; and
  (c) contacting the cell comprising the first DNA and the second DNA with a bacteriophage lambda integrase Int under conditions supporting sequence-specific integrase-mediated recombination, wherein the second DNA is integrated into the first DNA; and
  (d) cultivating the cell comprising the first DNA and the second DNA and the Int in a cellular culture medium under conditions, wherein the polypeptide of interest is produced.

9. The method according to claim 8, wherein the first DNA is integrated into an artificial chromosome, a minichromosome, an episomal element or the genome of said cell, in the cell prior to step (a).

10. The method according to claim 9, wherein the first DNA has been integrated into the cell genome in step (a).

11. The method according to claim 8, wherein said polypeptide of interest is isolated from the cultivated cell or the cell culture medium.

12. The method according to claim 1, wherein the first and/or the second DNA further comprises a nucleic acid coding for a polypeptide of interest operably linked to an expression control sequence.

13. The method according to claim 1 or claim 8, wherein the providing the Int to said cell comprises introducing a third DNA encoding the Int, or a third and a fourth DNA encoding the Int and one or more cofactors selected from XIS, FIS and/or IHF.

14. The method according to claim 1 or claim 8, wherein cofactors XIS, FIS and IHF are not employed and the Int is a modified Int.

15. The method according to claim 1 or 8, wherein the eukaryotic cell is a mammalian cell.

16. The method according to claim 15, wherein the mammalian cell is a rodent cell.

17. The method according to claim 16, wherein the rodent cell is a mouse or a hamster cell.

18. The method according to claim 17, wherein the hamster cell is a BHK or CHO cell.

19. The method according to claim 17, wherein the mouse cell is a murine myeloma cell.

20. The method according to claim 19, wherein the murine myeloma cell is a NSO or an Sp2/0 cell.

21. The method according to claim 8 or claim 12, wherein said polypeptide of interest is an antibody, a hormone or a growth factor.

* * * * *

UNITED STATES PATENT AND TRADEMARK OFFICE
CERTIFICATE OF CORRECTION

| | | |
|---|---|---|
| PATENT NO. | : 7,846,732 B2 | Page 1 of 1 |
| APPLICATION NO. | : 11/281945 | |
| DATED | : December 7, 2010 | |
| INVENTOR(S) | : Peter Droge et al. | |

It is certified that error appears in the above-identified patent and that said Letters Patent is hereby corrected as shown below:

In title page, item (63) Related U.S. Application Data, insert
--Continuation of application No. 10/310,695, filed on Dec. 5, 2002, now Pat. No. 7,491,539.--.

Signed and Sealed this
Fifteenth Day of March, 2011

David J. Kappos
*Director of the United States Patent and Trademark Office*

SEQUENCE LISTING

```
<160> NUMBER OF SEQ ID NOS: 22

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (1)
<223> OTHER INFORMATION: M = C or A

<400> SEQUENCE: 1 magtcactat                                                              10

<210> SEQ ID NO 2
<211> LENGTH: 243
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
tctgttacag gtcactaata ccatctaagt agttgattca tagtgactgc atatcttgtg      60
ttttacagta ttatctagtc tgtttttat ccaaaatcta atttaatata ttgatattta      120
tatcatttta cgtttctcgt tcagcttttt tatactaagt tggcattata aaaaagcatt     180
gcttatcaat ttgttgcaac gaacaggtca ctatcagtca aaataaaatc attatttgat     240
ttc                                                                    243

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
gtcactatca gtcaaaatac aatca                                            25

<210> SEQ ID NO 4
```

-continued

```
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
tgattgtatt ttgactgata gtgac                                           25

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ccaatgcatc ctctgttaca ggtcactaat ac                                   32

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ataagaatgc ggccgcagat atcagggagt gggacaaaat tgaa                      44

<210> SEQ ID NO 7
<211> LENGTH: 55
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
tttggataaa aaacagacta gataatactg taaaacacaa gatatgcagt cacta          55

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
taacgcttac aatttacgcg t                                               21

<210> SEQ ID NO 9
<211> LENGTH: 55
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
ctgcatatct tgtgttttac agtattatct agtctgtttt ttatccaaaa tctaa          55

<210> SEQ ID NO 10
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ctggacgtag ccttcgggca tggc                                          24

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
gactgctgca gctctgttac aggtcac                                       27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
gactgtctag agaaatcaaa taatgat                                       27

<210> SEQ ID NO 13
<211> LENGTH: 21
<212> TYPE: DNA
<213> ORGANISM: Escherichia coli

<400> SEQUENCE: 13 ctgcttttt atactaactt g                                              21

<210> SEQ ID NO 14
<211> LENGTH: 243
<212> TYPE: DNA
<213> ORGANISM: Bacteriophage lambda

<400> SEQUENCE: 14
tctgttacag gtcactaata ccatctaagt agttgattca tagtgactgc atatgttgtg     60
ttttacagta ttatgtagtc tgttttttat gcaaaatcta atttaatata ttgatattta    120
tatcatttta cgtttctcgt tcagcttttt tatactaagt tggcattata aaaaagcatt    180
gcttatcaat ttgttgcaac gaacaggtca ctatcagtca aaataaaatc attatttgat    240
ttc                                                                 243

<210> SEQ ID NO 15
<211> LENGTH: 102
<212> TYPE: DNA
<213> ORGANISM: Escherichia coli

<400> SEQUENCE: 15 ctgcttttt atactaagtt ggcattataa aaaagcattg cttatcaatt tgttgcaacg     60
aacaggtcac tatcagtcaa aataaaatca ttatttgatt tc                      102

<210> SEQ ID NO 16
<211> LENGTH: 162
```

```
<212> TYPE: DNA
<213> ORGANISM: Escherichia coli

<400> SEQUENCE: 16
tctgttacag gtcactaata ccatctaagt agttgattca tagtgactgc atatgttgtg      60
ttttacagta ttatgtagtc tgttttttat gcaaaatcta atttaatata ttgatattta    120
tatcatttta cgtttctcgt tcagcttttt tatactaact tg                       162

<210> SEQ ID NO 17
<211> LENGTH: 27
<212> TYPE: DNA
<213> ORGANISM: Homo sapiens

<400> SEQUENCE: 17
gaaattcttt ttgatactaa cttgtgt                                         27

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18 ctgctttt                                                               9

<210> SEQ ID NO 19
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19 caagttagt                                                              9

<210> SEQ ID NO 20
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20 cagctttt                                                               9

<210> SEQ ID NO 21
<211> LENGTH: 9
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21 caacttagt                                                              9

<210> SEQ ID NO 22
<211> LENGTH: 7
<212> TYPE: DNA
<213> ORGANISM: Artificial Sequence
<220> FEATURE:
```

```
-continued

<223> OTHER INFORMATION: Description of Artificial Sequence:  Synthetic
      Primer

<400> SEQUENCE: 22 tttatac                                                                  7
```